(12) United States Patent
Rodgers et al.

(10) Patent No.: US 7,786,085 B2
(45) Date of Patent: *Aug. 31, 2010

(54) METHOD FOR TREATING A PATIENT UNDERGOING CHEMOTHERAPY

(75) Inventors: Kathleen Rodgers, Long Beach, CA (US); Gere DiZerega, San Luis Obispo, CA (US)

(73) Assignee: University of Southern California, Los Angeles, CA (US)

(*) Notice: Subject to any disclaimer, the term of this patent is extended or adjusted under 35 U.S.C. 154(b) by 79 days.

This patent is subject to a terminal disclaimer.

(21) Appl. No.: 12/013,209

(22) Filed: Jan. 11, 2008

(65) Prior Publication Data

US 2008/0167252 A1 Jul. 10, 2008

Related U.S. Application Data

(63) Continuation of application No. 10/842,877, filed on May 10, 2004, now Pat. No. 7,338,938, which is a continuation of application No. 09/723,197, filed on Nov. 27, 2000, now Pat. No. 6,762,167, and a continuation-in-part of application No. 09/307,940, filed on May 10, 1999, now Pat. No. 6,475,988.

(60) Provisional application No. 60/201,470, filed on May 3, 2000, provisional application No. 60/220,804, filed on Jul. 25, 2000, provisional application No. 60/233,375, filed on Sep. 18, 2000, provisional application No. 60/235,040, filed on Sep. 25, 2000, provisional application No. 60/243,955, filed on Oct. 27, 2000.

(51) Int. Cl.
*A61K 38/08* (2006.01)
*C07K 7/06* (2006.01)

(52) U.S. Cl. .................. 514/16; 514/17; 424/9.1; 530/328; 530/329; 530/316; 435/325; 435/375

(58) Field of Classification Search ............ 435/16, 435/17, 325, 375; 424/9.1; 530/316, 328, 530/329

See application file for complete search history.

(56) References Cited

U.S. PATENT DOCUMENTS

| | | | |
|---|---|---|---|
| 5,015,629 A | 5/1991 | DiZerega | |
| 5,595,973 A | 1/1997 | Bogden | |
| 5,605,931 A | 2/1997 | Hanson | |
| 5,629,292 A | 5/1997 | Rodgers | |
| 5,693,616 A | 12/1997 | Krstenansky et al. | |
| 5,716,935 A | 2/1998 | Rodgers et al. | |
| 5,834,432 A | 11/1998 | Rodgers et al. | |
| 5,955,430 A | 9/1999 | Rodgers | |
| 6,335,195 B1 | 1/2002 | Rodgers et al. | |
| 6,455,500 B1 | 9/2002 | Rodgers et al. | |
| 6,475,988 B1 | 11/2002 | Rodgers et al. | |
| 6,566,335 B1 * | 5/2003 | Rodgers et al. | 514/15 |
| 6,762,167 B1 | 7/2004 | Rodgers et al. | |
| 6,821,953 B1 * | 11/2004 | Rodgers et al. | 514/16 |
| 7,118,748 B1 | 10/2006 | Rodgers et al. | |
| 7,173,011 B2 | 2/2007 | Rodgers et al. | |
| 7,176,183 B2 | 2/2007 | Rodgers et al. | |
| 7,338,938 B2 | 3/2008 | Rodgers et al. | |
| 2008/0039363 A1 | 2/2008 | Rodgers et al. | |

FOREIGN PATENT DOCUMENTS

| | | |
|---|---|---|
| WO | 9508337 | 3/1995 |
| WO | 9508565 | 3/1995 |
| WO | 9614858 | 5/1996 |
| WO | 9615795 | 5/1996 |
| WO | 9639164 | 12/1996 |
| WO | 9640090 | 12/1996 |
| WO | 9727867 | 8/1997 |
| WO | 9734627 | 9/1997 |
| WO | 9826795 | 6/1998 |
| WO | 9832457 | 7/1998 |
| WO | 9833813 | 8/1998 |
| WO | 9945945 | 9/1999 |

OTHER PUBLICATIONS

Bell et al., (1990) Am. J. Pathol., "Rapid Communication: Influence of the angiotensin system on endothelia and smooth muscle cell migration," vol. 137, pp. 7-12.

Berk et al., (1989) Hypertension, "Angiotensin 11-stimulated protein synthesis in cultured vascular smooth muscle cells", vol. 13, pp. 305-314.

Bryson et al., (1992), Eur. J. Pharrnacol., "Induction of the angiotensin AT2 receptor subtype expression by differentiation of the neuroblastoma X glioma hybrid, NG-108-IS", vol. 225, pp. 119-127.

Felipe G. Elizondo, Jr. and Cynthia Sung, "Effect of Angiotensin II on Immunotoxin Uptake in Tumor and Normal Tissue," Cancer Chemotherapy Pharmacology, vol. 39, (1996), pp. 94-97.

Catalioto et al. (1994) Eur. J. Pharmacol, "Angiotensins induce the release of prostacyclin from rabbit vas deferens: evidence for receptor heterogeneity", vol. 256, pp. 93-97.

(Continued)

*Primary Examiner*—Chih-Min Kam
(74) *Attorney, Agent, or Firm*—McDonnell Boehnen Hulbert & Berghoff LLP

(57) ABSTRACT

The present invention provides improved methods, kits, and pharmaceutical compositions for increasing hematopoietic cell survival and/or reducing or preventing the side effects of chemotherapy, and mobilizing hematopoietic progenitor cells from bone marrow into peripheral blood following chemotherapy, comprising administering an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists to a patient in need of chemotherapy.

18 Claims, 43 Drawing Sheets

OTHER PUBLICATIONS

Clouston et al., (1988) Genomics, "Molecular cloning of the mouse angiotensinogen gene", vol. 2, pp. 240-248.

Dworkin, et al., (1997), British Journal of Cancer, "Effect of ccintinuous regional vasoactive agent infusion on liver metastatsis blood flow", vol. 76(9), pp. 1205-1210.

Dzau et al., (1989) J. Mol. Cell Cardiol., "Molecular mechanism of angiotensin in the regulation of vascular and cardiac growth", vol. 21, (Supplement III) pp. S7.

Edwards et al. (1993) J. Pharmacol. Exper. Ther., "Angiotensin II inhibits glomerular adenylate cyclase via the angiotensin 11 receptor subtype 1 (ATI)", vol. 266, pp. 506-510.

Fernandez et al., (1985) J. Lab. Clin. Med., "Neovascularization produced by angiotensin II", vol. 105 pp. 141-145.

Jaiswal et al. (1992) Hypertension , "Stimulation of endothelial cell prostaglandin production by angiotensin peptides", vol. 19 (Supp. PI):-II-49-II-55.

Jaiswal et al. (1993) 3: Pharmacol. Exper. Ther., "Differential regulation of prostaglandin synthesis by angiotensin prptides in porcine aortic smooth muscle cells: subtypes of angiotensin receptors involved", vol. 265, pp. 664-673.

Jaiswal et al. (1991) Hypertension, "Subtype 2 angiotensin receptors mediate prostaglandin synthesis in human astrocytes", vol. 17, pp. 11 15-1 120.

Janiak et al., (1992) Hypertension, "Role of angiotensin subtype 2 receptor in neointima formation after vascular injury", vol. 20, pp. 737-745.

Jimenez and Yunis, (1992), Cancer Research, "Protection from 1-β-D-Arabinofuranosylcytosine-induced Alopecia by Epidermal growth Factor and Fibroblast Growth Factor in the Rat Model", vol. 52, pp. 413-415.

Kageyama et al., (1984) Biochemistry, "Primary structure of human preangiotensinogen deduced from the cloned cDNA sequence", vol. 23, pp. 3603-3609.

Kauffinan et al., (1991), Life Sci., "Losartan, a nonpeptide angiotensin II (ANGPI) receptor antagonist, inhibits neointima formation following balloon injury to rat carotid arteries", Vol.49, pp. 223-228.

Kawahara, et al., (1988), BBRC, "Angiotensin II induces expression of the C-FOS gene through protein b a s e C activation and calcium ion mobilization in cultured vascular smooth muscle cells", vol. 150(1), pp. 52-59.

Kimurii, et al., (1992), BBRC, "Changes in skin angiotensin II receptors in rats during wound healing," vol.187, pp. 1083-1090.

Kuroiwa, et al., (1995), Cancer Chemother Pharmacol, Phase II study of a new combined primary chemotherapy regimen, intravenous methotrexate and vincristine and intraarterial adriamycin and cisplatin, for locally advanced urinary bladder cancer: preliminary results, vol. 35, pp. 357-363.

LeNoble, et a1.,(1991) Eur. J. Pharmacol., "Angiotensin II stimulates angiogenesis in the chorio-allantoic membrane of the chick embryo", vol. 195, pp. 305-306.

Li, et al., (1993), Br. J. Cancer, "Augmentation of tumour delivery of macromolecular drugs with reduced bone marrow delivery by elevating blood pressure", vol. 67, pp. 975-980.

Morita, et al., (1992), Am. J. Clin. Oncol., Intraarterial infusion chemotherapy with [Sar1,Ile8]: 15, pp. 188-193.

Mrug, M., et al., (1997), J. Clin. Invest., vol. 100, pp. 2310-2314.

Mutoh, et al., (1992), Urol Int., "Local control of prostate cancer by intraarterial infusion chemotherapy facilitated by the use of angiotensin II", vol. 48, pp. 175-180.

Naftilan, et al., (1989), J. Clin. Invest., "Induction of plaalet-derived growth factor A-chain and c-myc gene expressions by angiotensin 11 in cultured rat vascular smooth muscle cells", vol. 83, pp. 1419-1423.

Nakahara et al., (1992) BBRC, "Identification of three types of PDGF-A chain gene transcripts in rabbit vascular smooth muscle and their regulated expression during development and by angiotensin II", vol. 184, pp. 8 11-818.

Ohigashi, et al., (1996), Hepato-Gastroenterology, "A new method of intra-arterial regional chemotherapy with more selective drug delivery for locally advanced pancreatic cancer", vol. 43, pp. 338-345.

Ohkubo et al., (1983) Proc. Natl. Acad. Sci., "Cloning and sequence analysis of cDNA for rat angiotensinogen", vol. 80, pp. 2196-2200.

Pfeilschifter et al. (1992) Eur. J. Pharmacol., "Angiotensin II stimulation of phospholipase D in rat renal mesangial cells is mediated by the AT1 receptor subtype", vol. 225, pp. 57-62.

Portsi et al. (1994) Br. J. Pharmacol., "Release of nitric oxide by angiotensin-(1-7) from porcine coronary endothelium: implications for a novel angiotensin", vol. 111, pp. 652-654.

Prescott et al., (1991) Am J: Pathol., "Angiotensin-converting enzyme inhibitor versus angiotensin II, AT1 receptor antagonist", vol. 139, pp. 1291-1296.

Regoli et al., (1974), Pharmacological Reviews, "Pharmacology of angiotensiny," vol. 26,pp. 69-123.

Sato, et al., (1995), World J. Surg., "Angiotensin II (AII) induced hypertension chemotherapy (IHC) for unresectable gastric cancer: With reference to resection after down staging", vol. 19, pp. 836-742.

Speth, et al., (1990), Biochemical and Biophysical Research Communications, "Discrimination of two angiotensin II receptor subtypes with a selective agonist analogue of angiotensin II, p-aminophenylalanine6 angiotensin II," vol. 169 (3), pp. 997-1006.

Stouffer et al., (1992) Circ. Res., "Angiotensin II-induced mitogenesis of spontaneously hypertensive rat-dericed cultured smooth muscle cells is dependent on autocrine production of transforming growth factor-B", vol. 70, pp. 820-828.

Taniguchi, et al., (1996), J. Nuclear Medicine, "Angiotensin-II-induced hypertension chemotherapy: Evaluation of hepatic blood flow with oxygen-15 PET", vol. 37, pp. 1522-1523.

Taubman et al. (1989) J. Biol. Chem., "Angiotensin II induces c-fos mRNA in aortic smooth muscle", vol. 264, pp. 526-530.

Tubiana, M., et al., (1993), Radiotherapy and Oncology, "Ways of minimizing hematopoietic damage induced by radiation and cytostatic drugs-the possible role of inhibitors", vol. 29, pp. 1-17.

Viswanathan, et a1., (1992), Peptides, "Expression of angiotensin II AT2 receptors in the rat skin during experimental wound healing", vol. 13, pp. 783-786.

Wolf et al., (1992) Am. J. Pathol., "Angiotensin II stimulates the proliferation and biosynthesis of type I collagen in cultured murine mesangial cells", vol. 140, pp. 95-107.

\* cited by examiner

Effect of Angiotensin II on White Blood Cell Number

Effect of AII on WBC after Chemotherapy

Effect of 2GD on WBC after Chemotherapy

Effect of 5GD on WBC after Chemotherapy

Effect of 9GD on WBC after Chemotherapy

Effect of Angiotensin Peptides on GM-CFU

Effect of Angiotensin Peptides on GM-CFU

Effect of Angiotensin Peptides on GM-CFU

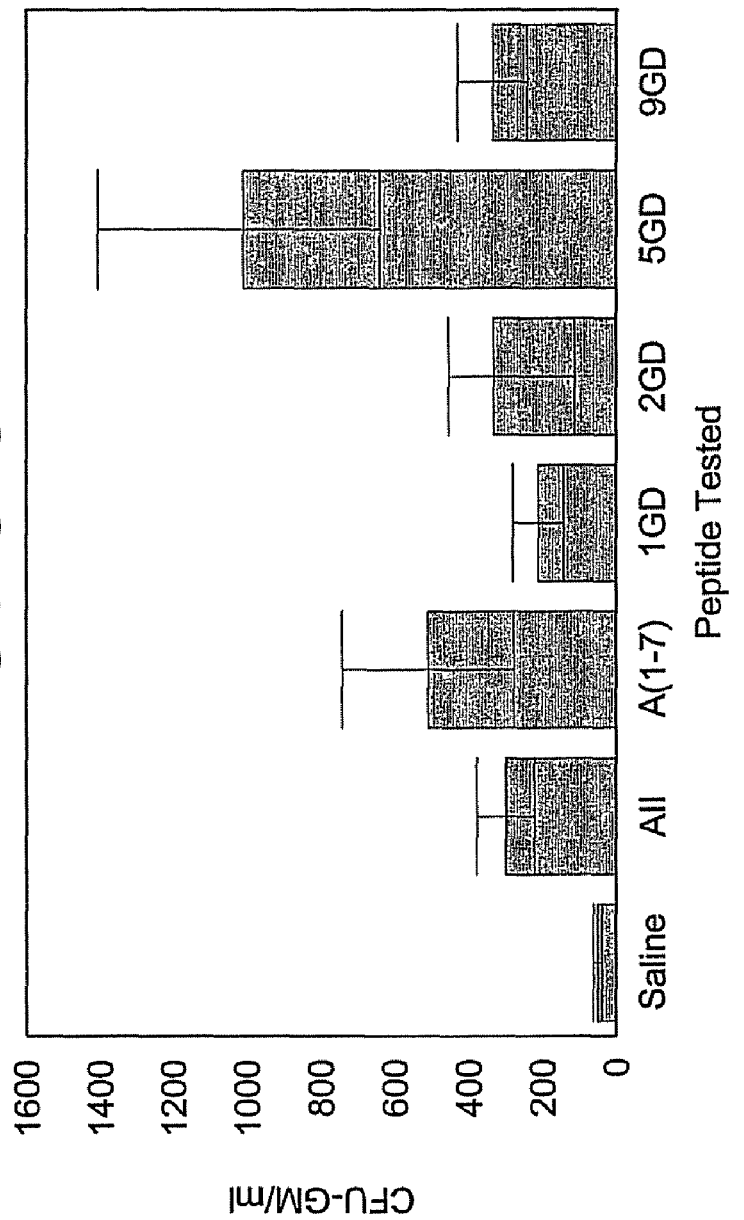

Effect of A(1-7) on Hematopoietic Recovery after Cytoxan Chemotherapy

Initiated Day +2

Effect of A(1-7) on Hematopoietic Recovery after Cytoxan Chemotherapy

Initiated Day -2

Effect of A(1-7) on Hematopoietic Recovery after Cytoxan Chemotherapy

SEQUENCE LISTING

```
<160> NUMBER OF SEQ ID NOS: 42

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Arg Val Tyr Ile His Pro
 1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 5

Arg Val Tyr Ile His Pro
  1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Val Tyr Ile His Pro
  1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ile His Pro Phe
  1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Arg Val Tyr Ile His
  1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asp Arg Val Tyr Ile
  1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Synthetic
```

```
<400> SEQUENCE: 11

Asp Arg Val
  1

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
  1               5

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Tyr Ile His Pro Phe
  1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: UNSURE
```

```
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
  1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Arg Val Tyr Gly His Pro Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Arg Val Tyr Ala His Pro Phe
  1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Asp Arg Val Tyr Val His Pro Phe
  1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Asn Arg Val Tyr Val His Pro Phe
  1               5

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Ala Pro Gly Asp Arg Ile Tyr Val His Pro Phe
  1               5                  10
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Asp Lys Val Tyr Ile His Pro Phe
 1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Asp Arg Val Tyr Ile Arg Pro Phe
 1               5
```

```
<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic

<400> SEQUENCE: 31

Asp Arg Pro Tyr Ile His Pro Phe
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)
<223> OTHER INFORMATION: Nle
```

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Asp Arg Val Tyr Ile His Pro Phe His Leu
 1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Asp Arg Pro Tyr Ile His Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Asp Arg Lys Tyr Ile His Pro
 1               5

<210> SEQ ID NO 41
<211> LENGTH: 7
<212> TYPE: PRT
<213> ORGANISM: Artificial Sequence
<220> FEATURE:
<221> NAME/KEY: MOD_RES
<222> LOCATION: (3)
<223> OTHER INFORMATION: Nle
<220> FEATURE:
<223> OTHER INFORMATION: Synthetic

<400> SEQUENCE: 41

Asp Arg Xaa Tyr Ile His Pro
 1               5

<210> SEQ ID NO 42
<211> LENGTH: 8
<212> TYPE: PRT
<213> ORGANISM: Artificial
<220> FEATURE:
<223> OTHER INFORMATION: Synthetic
<220> FEATURE:
<221> NAME/KEY: UNSURE
<222> LOCATION: (3)..(3)
<223> OTHER INFORMATION: Xaa is Val, Pro, Lys, NorLeu or Leu
<220> FEATURE:
<221> NAME/KEY: UNSURE
<222> LOCATION: (4)..(4)
<223> OTHER INFORMATION: Xaa is Ala, Tyr, or Tyr(PO3)2
<220> FEATURE:
<221> NAME/KEY: UNSURE
<222> LOCATION: (8)..(8)
<223> OTHER INFORMATION: Xaa is Phe or absent

<400> SEQUENCE: 42

Asp Arg Xaa Xaa Ile His Pro Xaa
 1               5

METHOD FOR TREATING A PATIENT UNDERGOING CHEMOTHERAPY

CROSS REFERENCE

This application is a continuation of U.S. patent application Ser. No. 10/842,877 filed May 10, 2004, now U.S. Pat. No. 7,338,938, which is a continuation of U.S. application Ser. No. 09/723,197, filed Nov. 27, 2000, now U.S. Pat. No. 6,762,167, which claims priority to U. S. Provisional Patent Application Nos: 60/201,470 filed May 3, 2000; 60/220,804 filed Jul. 25, 2000; 60/233,375 filed Sept. 18, 2000; 60/235, 040 filed Sept. 25, 2000; and 60/243,955 filed Oct. 27, 2000, and which is a Continuation-In-Part of U.S. patent application Ser. No. 09/307,940 filed May 10, 1999, now U.S. Pat. No. 6,475,988.

FIELD OF THE INVENTION

The present invention relates to methods, pharmaceutical compositions, and articles of manufacture for treating a patient undergoing chemotherapy, particularly for increasing hematopoietic cell survival and stem cell mobilization, and reducing the incidence and/or severity of chemotherapy-related side effects.

BACKGROUND OF THE INVENTION

People diagnosed as having cancer are frequently treated with single or multiple cytotoxic chemotherapeutic agents (cytotoxic agents) to kill cancer cells at the primary tumor site or at distant sites to where cancer has metastasized. (U.S. Pat. No. 5,605,931 incorporated by reference herein in its entirety.) Chemotherapy treatment is given either in a single or in several large doses or, more commonly, it is given in small doses 1 to 4 times a day over variable times of weeks to months. There are many cytotoxic agents used to treat cancer, and their mechanisms of action are generally poorly understood.

Irrespective of the mechanism, useful chemotherapeutic agents are known to injure and kill cells of both tumors and normal tissues. The successful use of chemotherapeutic agents to treat cancer depends upon the differential killing effect of the agent on cancer cells compared to its side effects on critical normal tissues. Among these effects are the killing of hematopoietic blood forming cells, and the killing and suppression of the white blood cells, which can lead to infection. Acute and chronic bone marrow toxicities are also major limiting factors in the treatment of cancer. They are both related to a decrease in the number of hemopoietic cells (e.g., pluripotent stem cells and other progenitor cells) caused by both a lethal effect of cytotoxic agents or radiation on these cells, and via differentiation of stem cells provoked by a feed-back mechanism induced by the depletion of more mature marrow compartments. (U.S. Pat. No. 5,595,973 incorporated by reference herein in its entirety.) Stimulators and inhibitors of bone marrow kinetics play a prominent role in the induction of damage and recovery patterns (Tubiana, M., et al., Radiotherapy and Oncology 29:1, 1993).

Prevention of, or protection from, the side effects of chemotherapy would be a great benefit to cancer patients. The many previous efforts to reduce these side effects have been largely unsuccessful. For life-threatening side effects, efforts have concentrated on altering the dose and schedules of the chemotherapeutic agent to reduce the side effects. Other options are becoming available, such as the use of granulocyte colony stimulating factor (G-CSF), granulocyte-macrophage-CSF (GM-CSF), epidermal growth factor (EGF), interleukin 11, erythropoietin, thrombopoietin, megakaryocyte development and growth factor, pixykines, stem cell factor, FLT-ligand, as well as interleukins 1, 3, 6, and 7, to increase the number of normal cells in various tissues before the start of chemotherapy (See Jimenez and Yunis, Cancer Research 52:413-415; 1992). The mechanisms of protection by these factors, while not fully understood, are most likely associated with an increase in the number of normal critical target cells before treatment with cytotoxic agents, and not with increased survival of cells following chemotherapy.

Acute myelosuppression as a consequence of cytotoxic chemotherapy is well recognized as a dose-limiting factor in cancer treatment. (U.S. Pat. No. 5,595,973) Although other normal tissues may be adversely affected, bone marrow is particularly sensitive to the proliferation-specific treatment such as chemotherapy or radiotherapy. For some cancer patients, hematopoietic toxicity frequently limits the opportunity for chemotherapy dose escalation. Repeated or high dose cycles of chemotherapy may be responsible for severe stem cell depletion leading to serious long-term hematopoietic sequelea and marrow exhaustion.

Despite advances in the field of chemotherapy, prior art methods have proven to be of limited utility in minimizing chemotherapy-induced depletion of hematopoietic stem cells and their progeny. Thus, there is a need for improved therapeutic methods and pharmaceutical compositions for increasing hematopoietic cell survival following chemotherapeutic treatments, as well as for decreasing the adverse effects of chemotherapy on the bone marrow.

SUMMARY OF THE INVENTION

In one aspect, the present invention provides methods, pharmaceutical compositions, and articles of manufacture for treating a patient undergoing chemotherapy, for increasing hematopoietic cell survival following chemotherapy, for reducing or preventing other side effects of chemotherapy, such as anemia, and for mobilizing hematopoietic progenitor cells from bone marrow into peripheral blood, comprising administering an amount effective for such purposes of angiotensinogen, angiotensin I (AI), AI analogues, AI fragments and analogues thereof, angiotensin II (AII), AII analogues, AII fragments or analogues thereof, AII $AT_2$ type 2 receptor agonists, or ACE inhibitors.

These aspects and other aspects of the invention become apparent in light of the following detailed description.

BRIEF DESCRIPTION OF THE DRAWINGS

FIG. 30 is a graph showing the effect of 100 μg AII and AII analogues and fragments on GM-CFU numbers in the blood on day 10 after 5FU treatment.

DETAILED DESCRIPTION OF THE PREFERRED EMBODIMENTS

Figure 1:
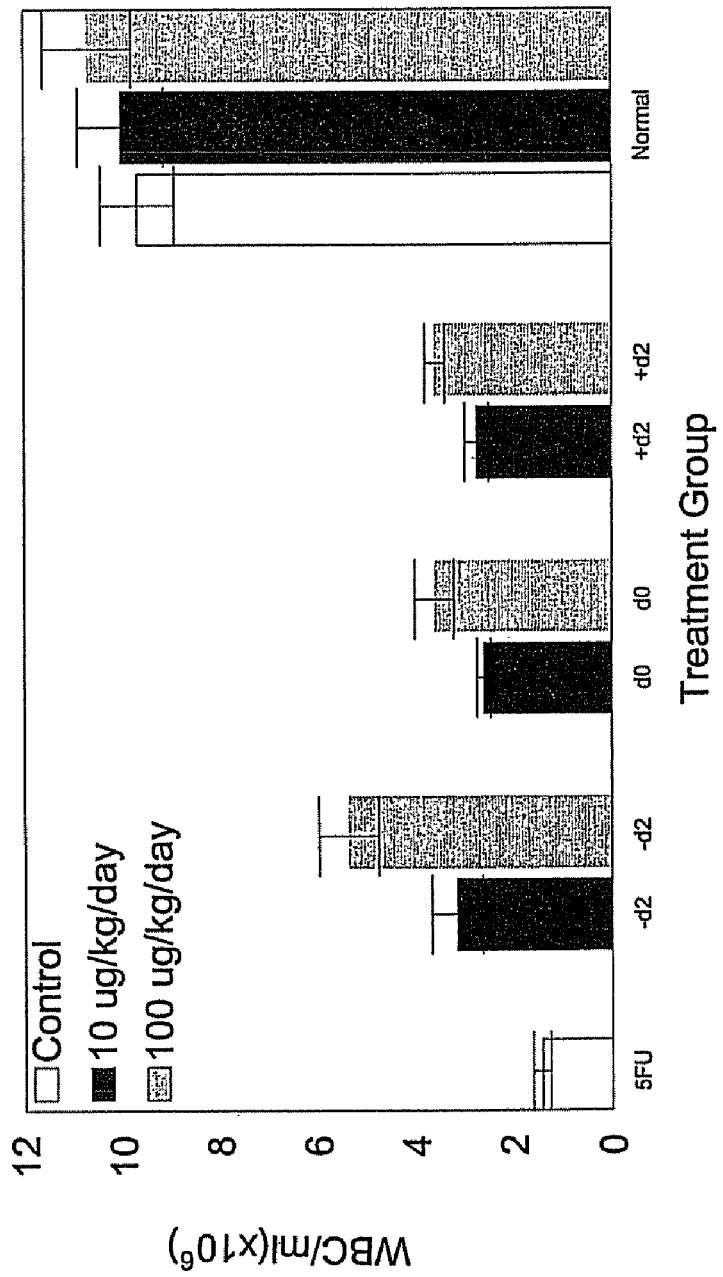
FIG. 1 is a graph showing the effect of AII treatment on white blood cell number in the blood 7 days after 5FU treatment.
Figure 2:
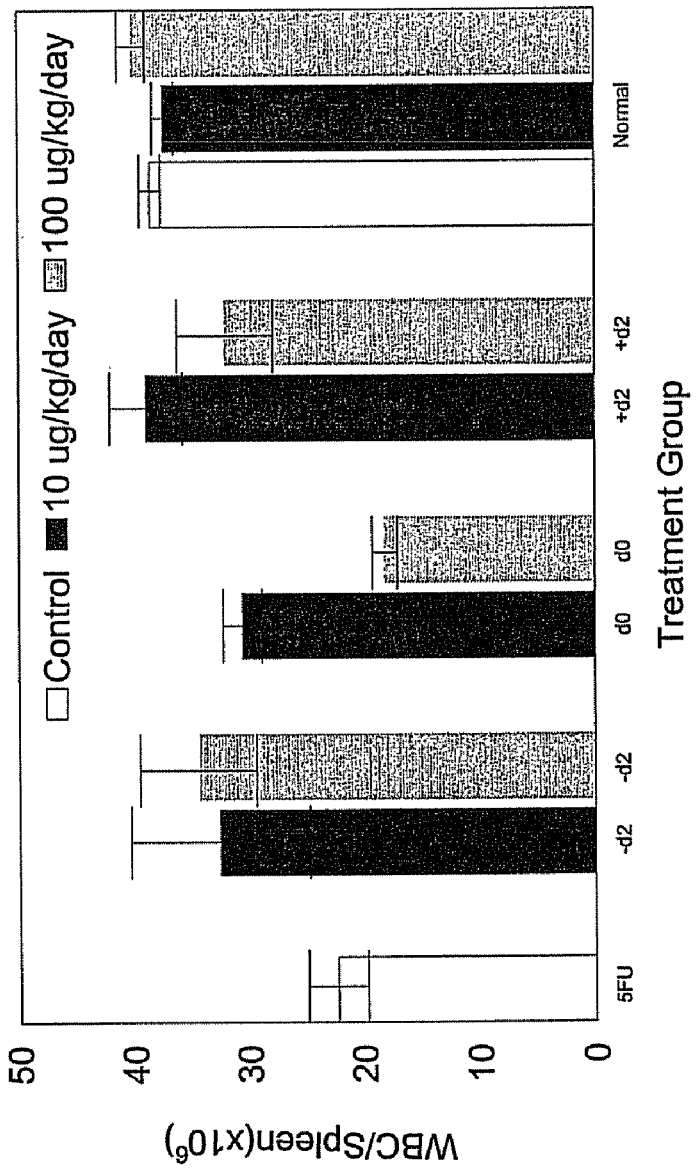
FIG. 2 is a graph showing the effect of AII treatment on white blood cell number in the spleen 7 days after 5FU treatment.
Figure 3:
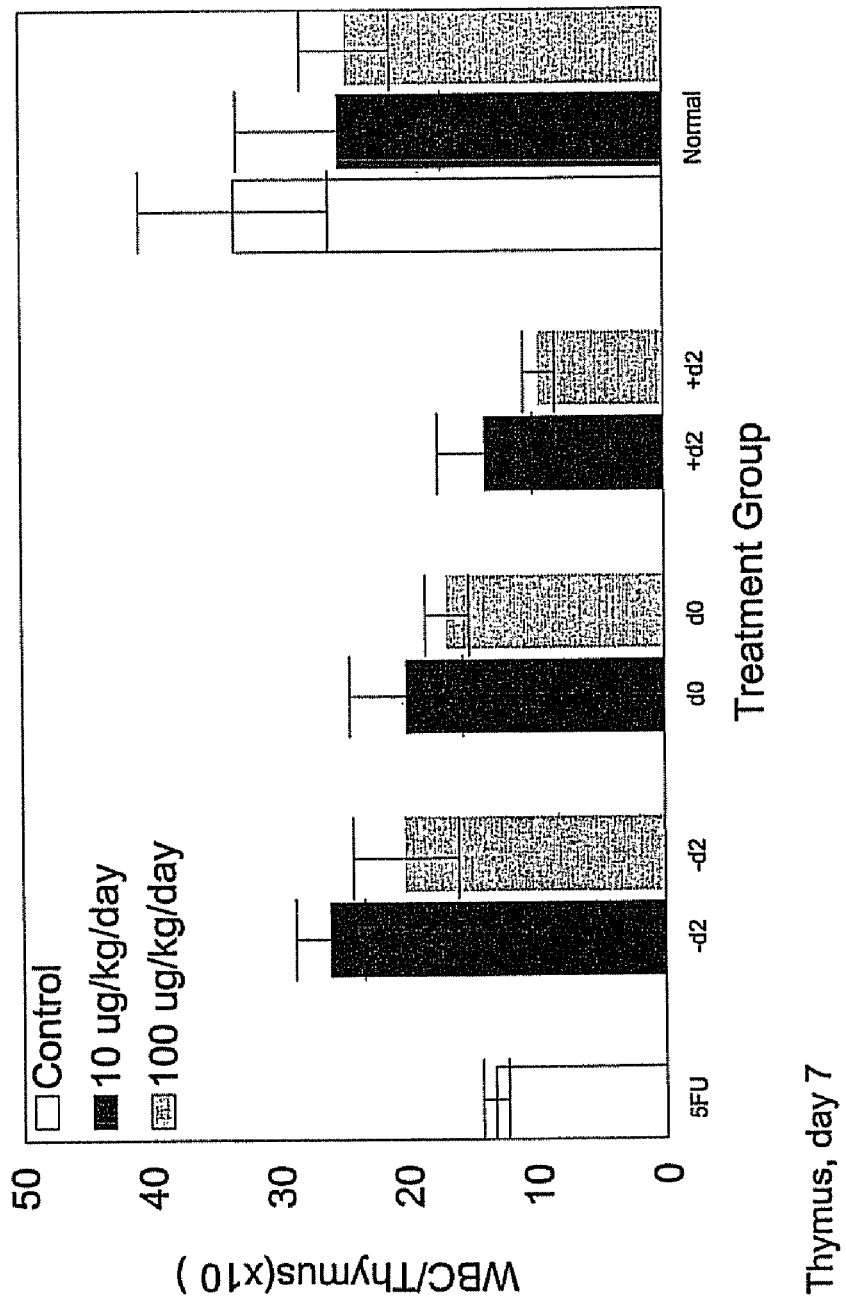
FIG. 3 is a graph showing the effect of AII treatment on white blood cell number in the thymus 7 days after 5FU treatment.
Figure 4:
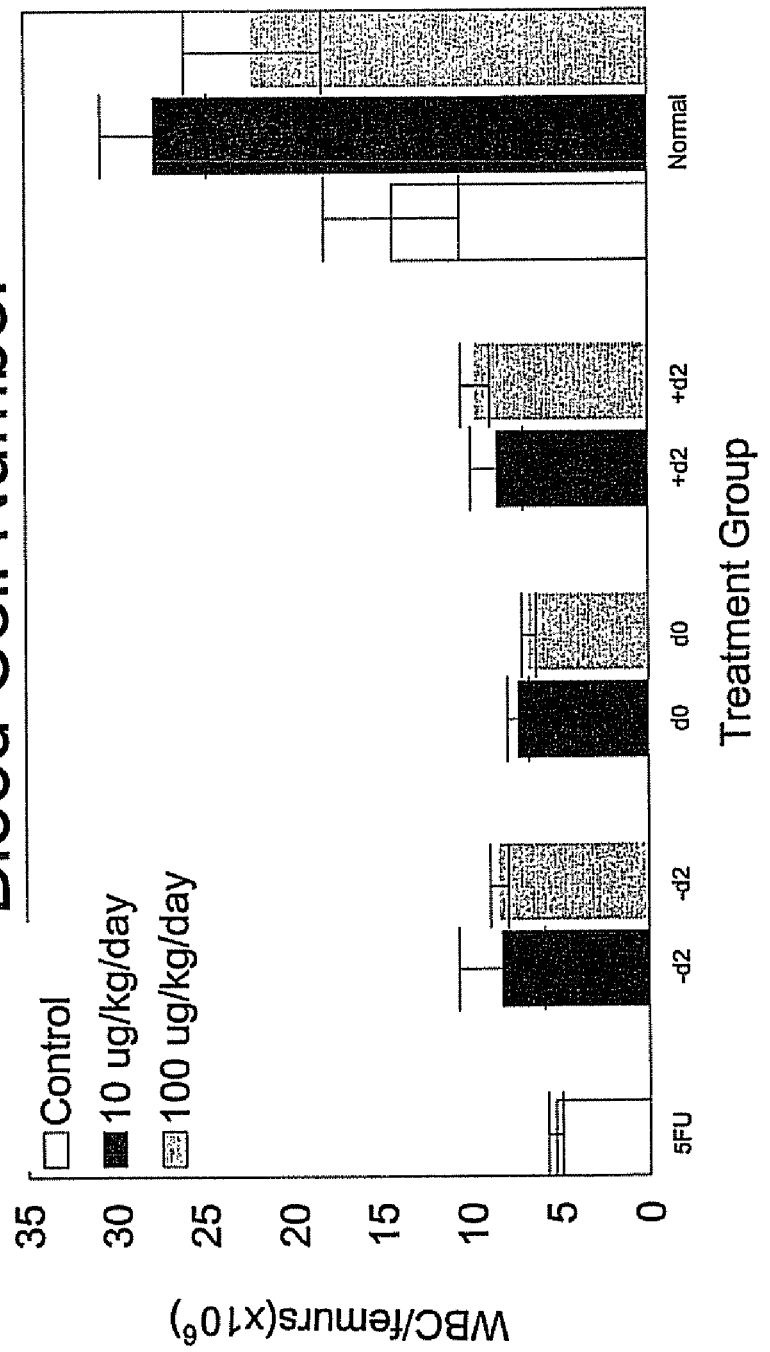
FIG. 4 is a graph showing the effect of AII treatment on white blood cell number in the bone marrow 7 days after 5FU treatment.
Figure 5:
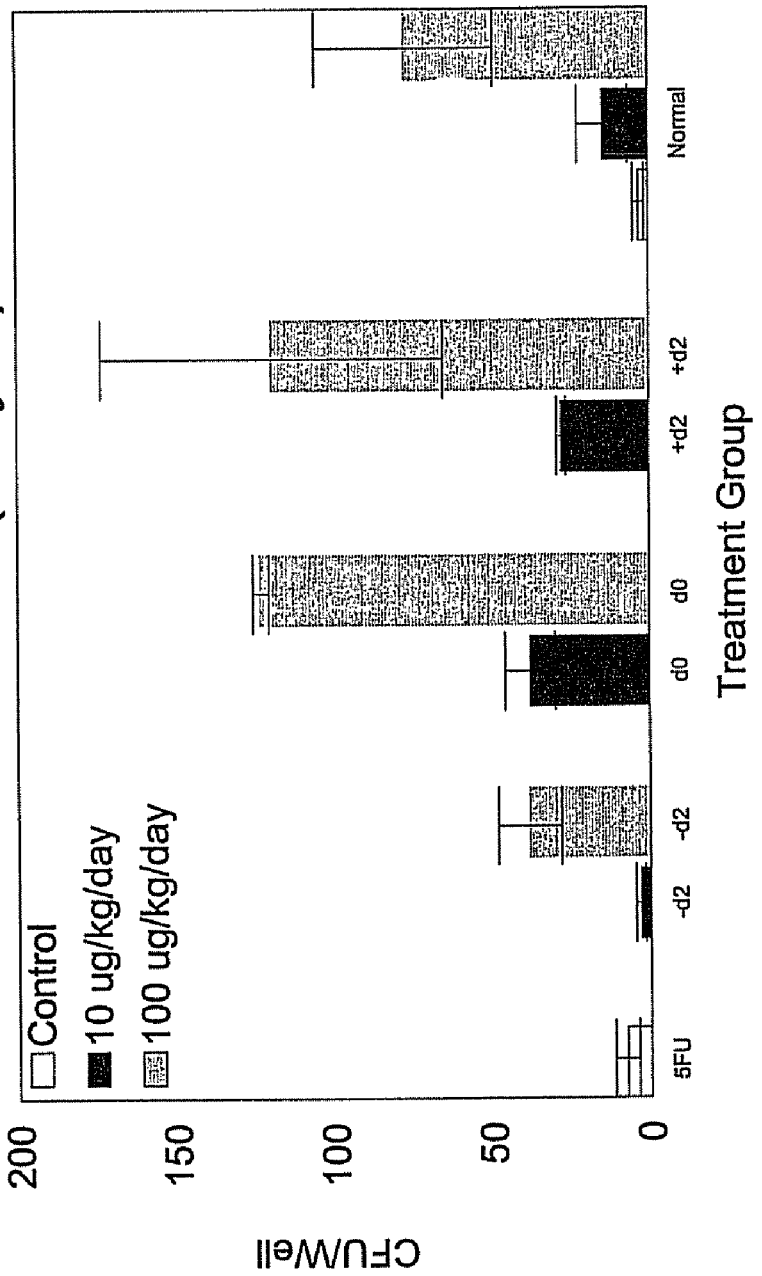
FIG. 5 is a graph showing the effect of AII treatment on CFU-GM cell number on day 7 after culture initiation following blood harvest 7 days after 5FU treatment.
Figure 6:
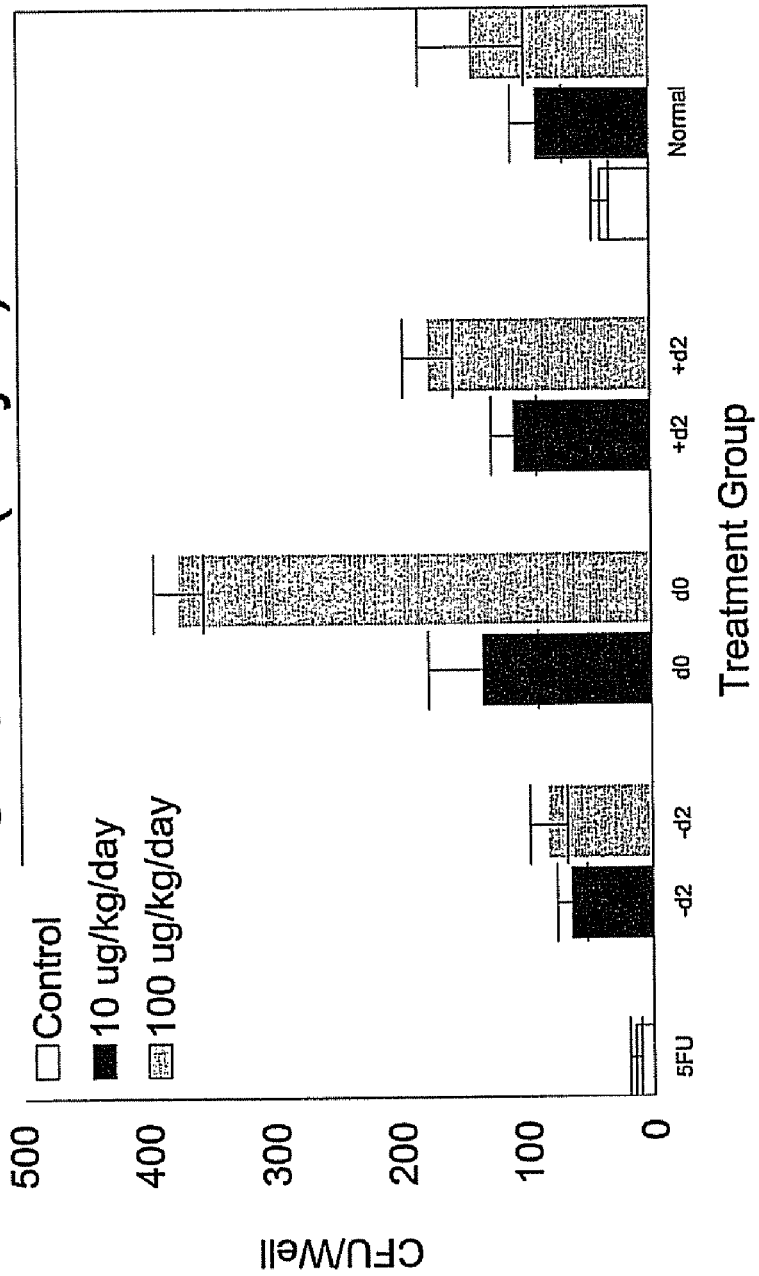
FIG. 6 is a graph showing the effect of AII treatment on CFU-GM cell number on day 7 after culture initiation following spleen harvest 7 days after 5FU treatment.
Figure 7:
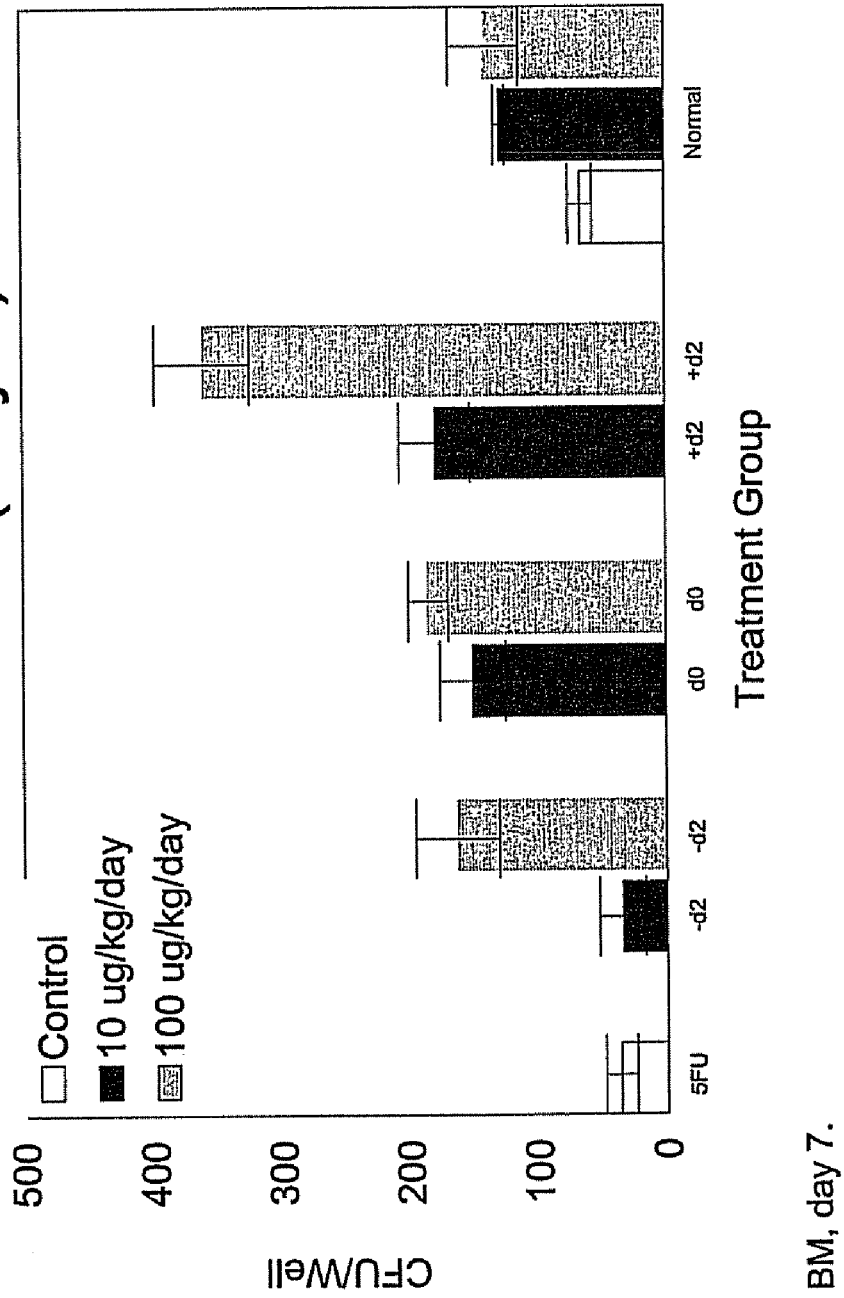
FIG. 7 is a graph showing the effect of AII treatment on CFU-GM cell number on day 7 after culture initiation following bone marrow harvest 7 days after 5FU treatment.
Figure 8:
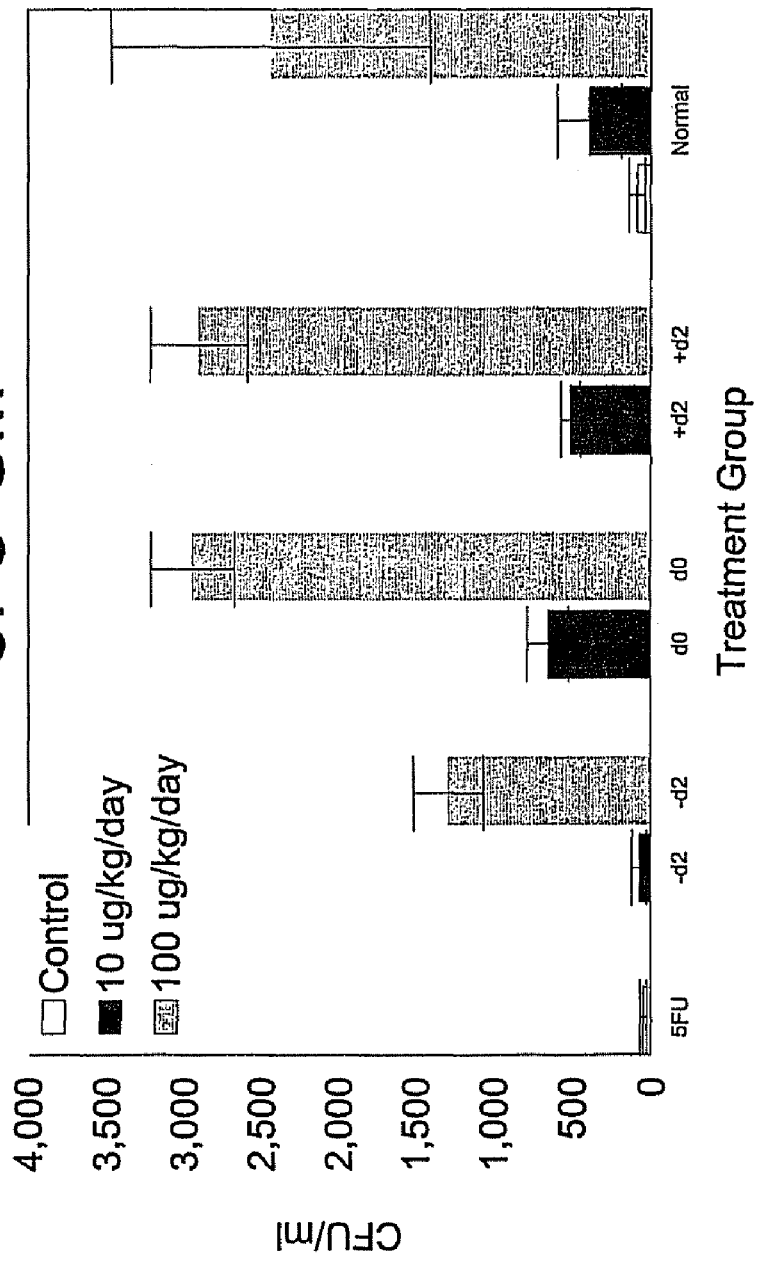
FIG. 8 is a graph showing the effect of AII treatment on CFU-GM cell number in the blood on day 7 after 5FU treatment.
Figure 9:
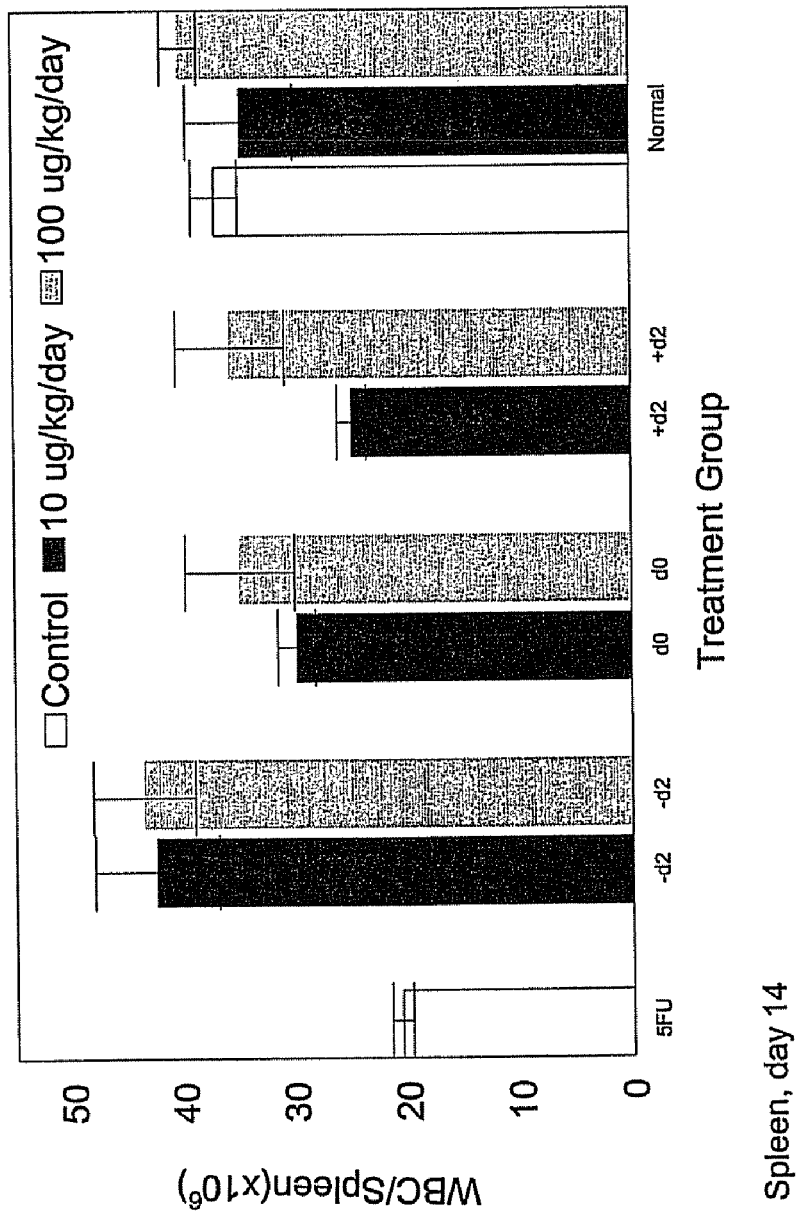
FIG. 9 is a graph showing the effect of AII treatment on white blood cell number in the spleen on day 14 after 5FU treatment.
Figure 10:
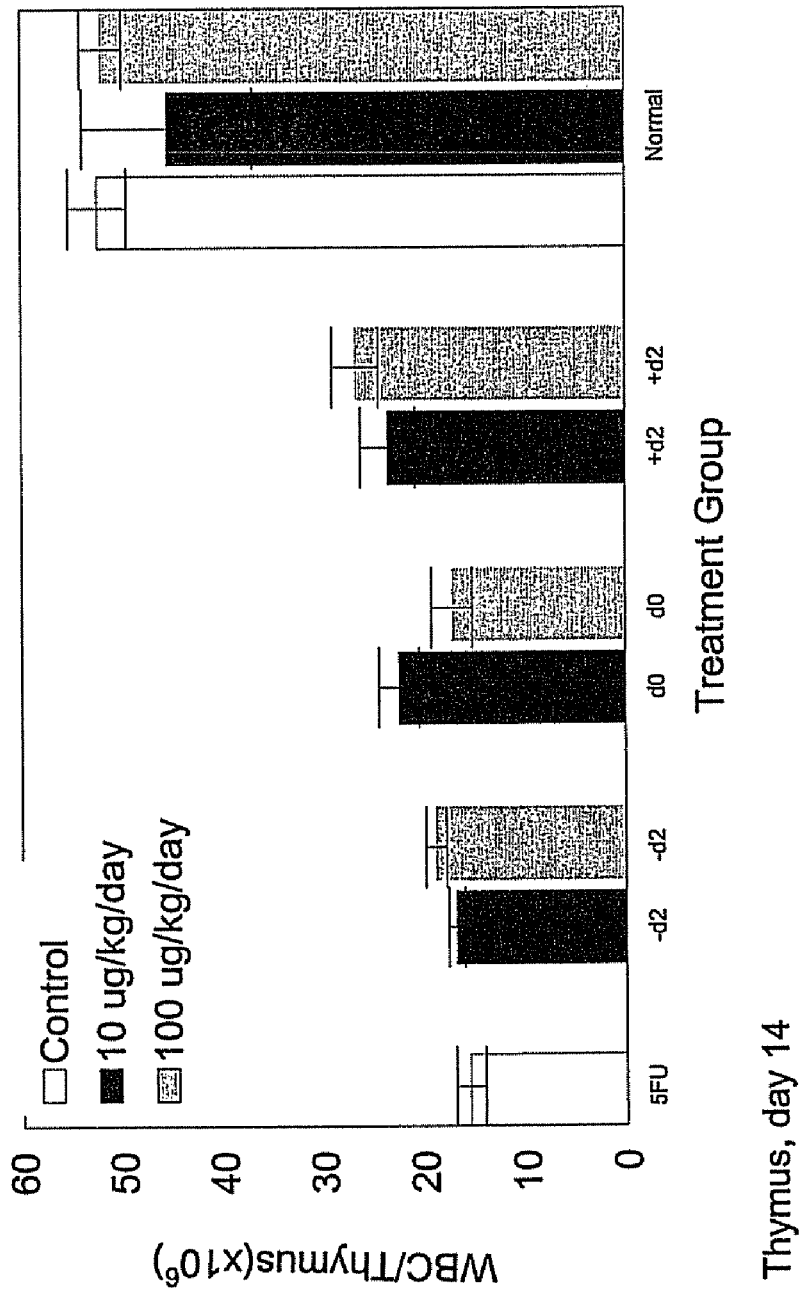
FIG. 10 is a graph showing the effect of AII treatment on white blood cell number in the thymus on day 14 after 5FU treatment.
Figure 11:
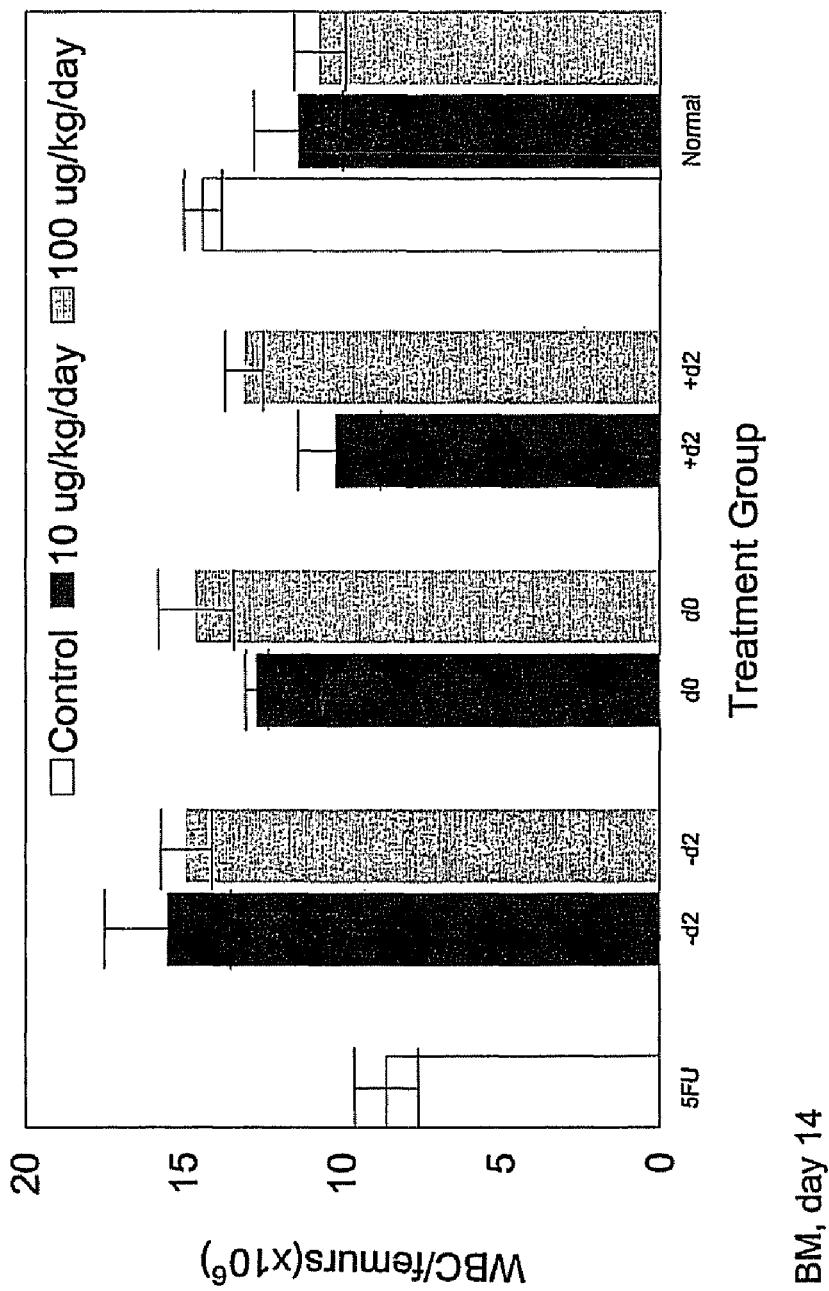
FIG. 11 is a graph showing the effect of AII treatment on white blood cell number in the bone marrow on day 14 after 5FU treatment.
Figure 12:
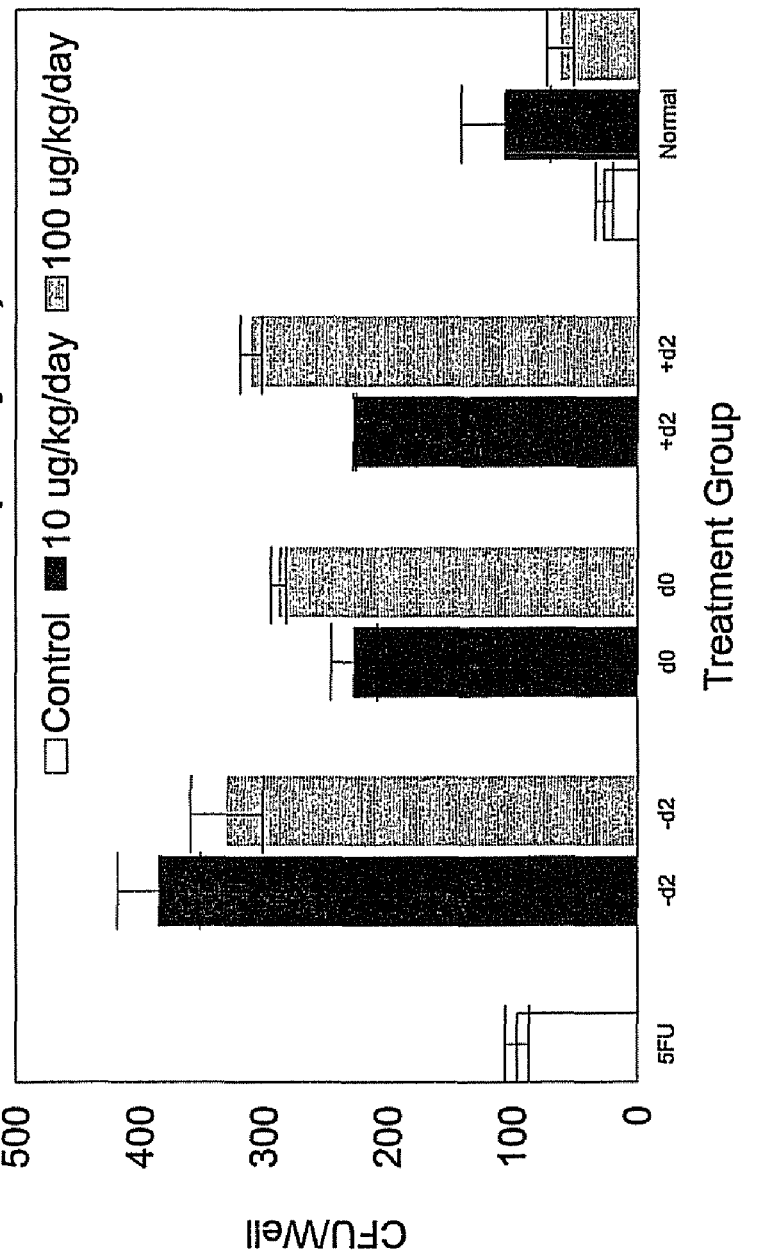
FIG. 12 is a graph showing the effect of AII treatment on CFU-GM cell number on day 7 after culture initiation following spleen harvest 14 days after 5FU treatment.
Figure 13:
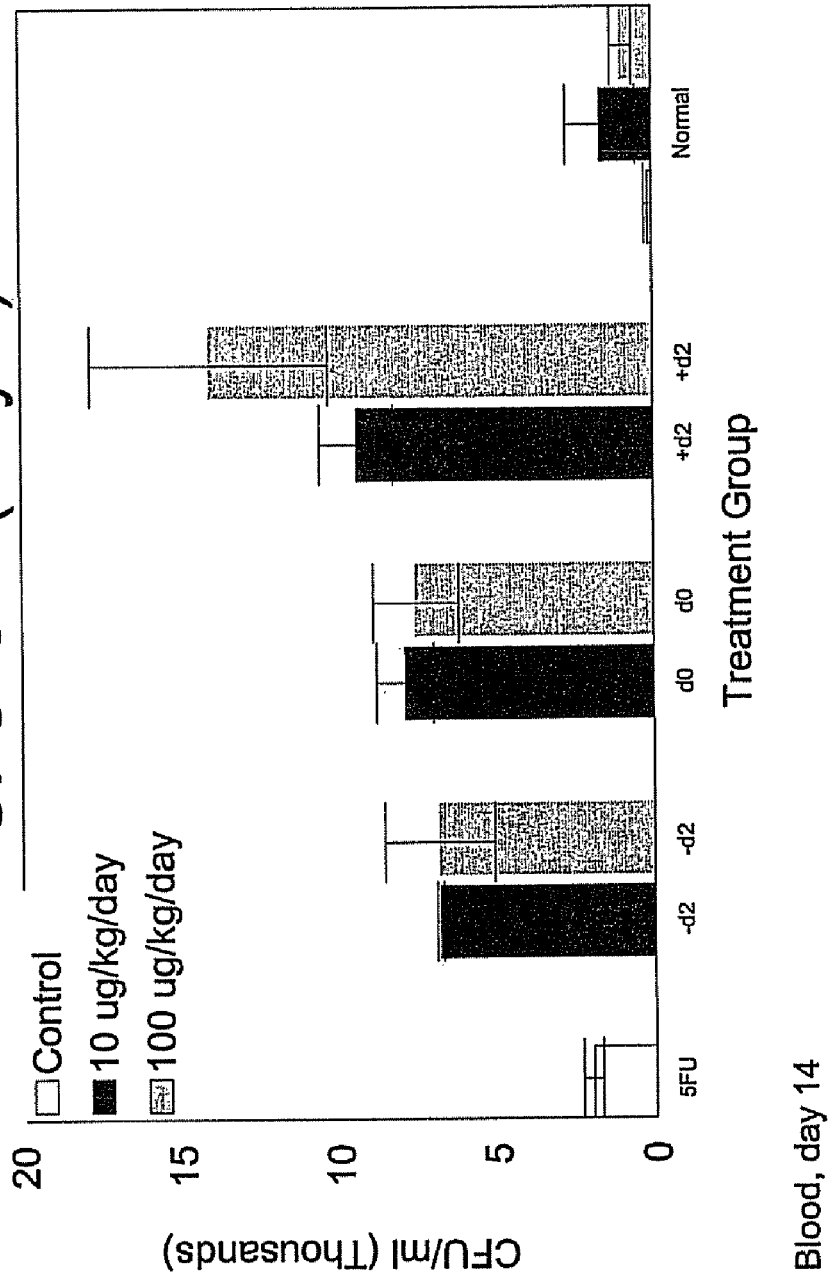
FIG. 13 is a graph showing the effect of AII treatment on CFU-GM cell number on day 7 after culture initiation following blood harvest 14 days after 5FU treatment.
Figure 14:
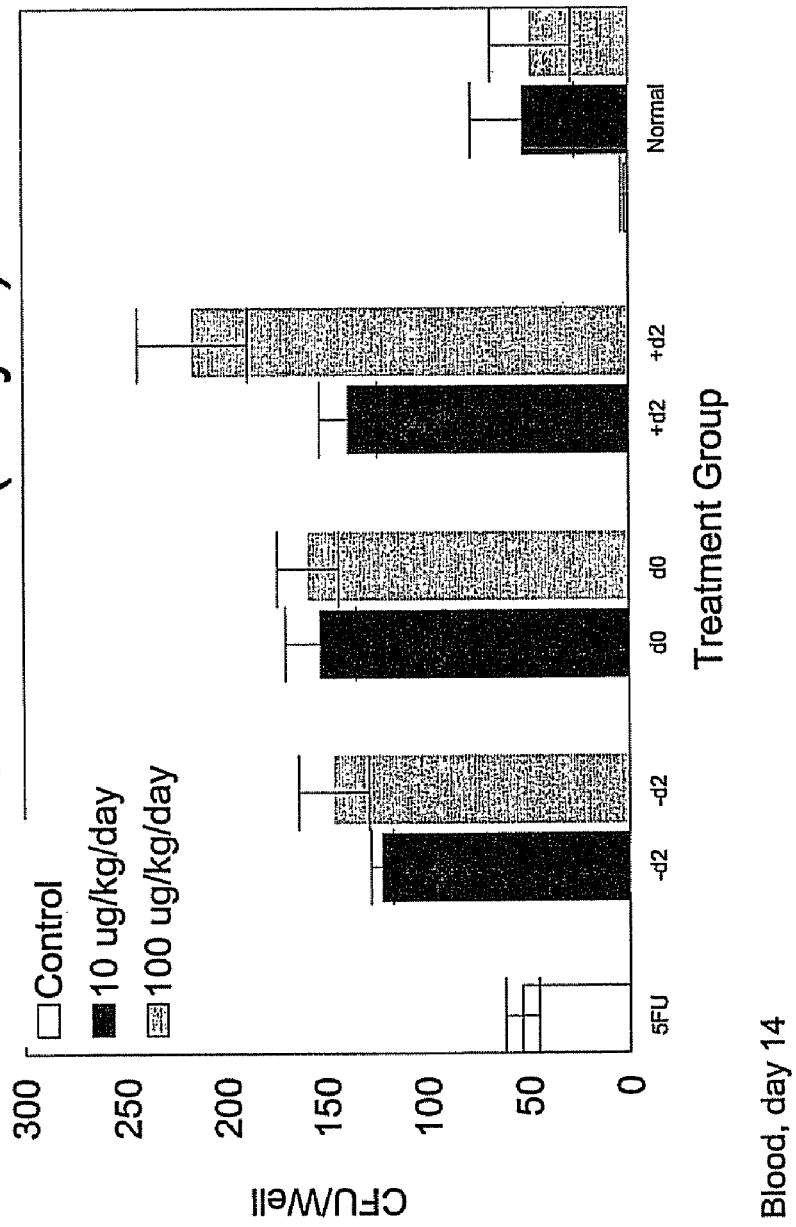
FIG. 14 is a graph showing the effect of AII treatment on CFU-GM cell number on day 7 after culture initiation following blood harvest 14 days after 5FU treatment.
Figure 15:
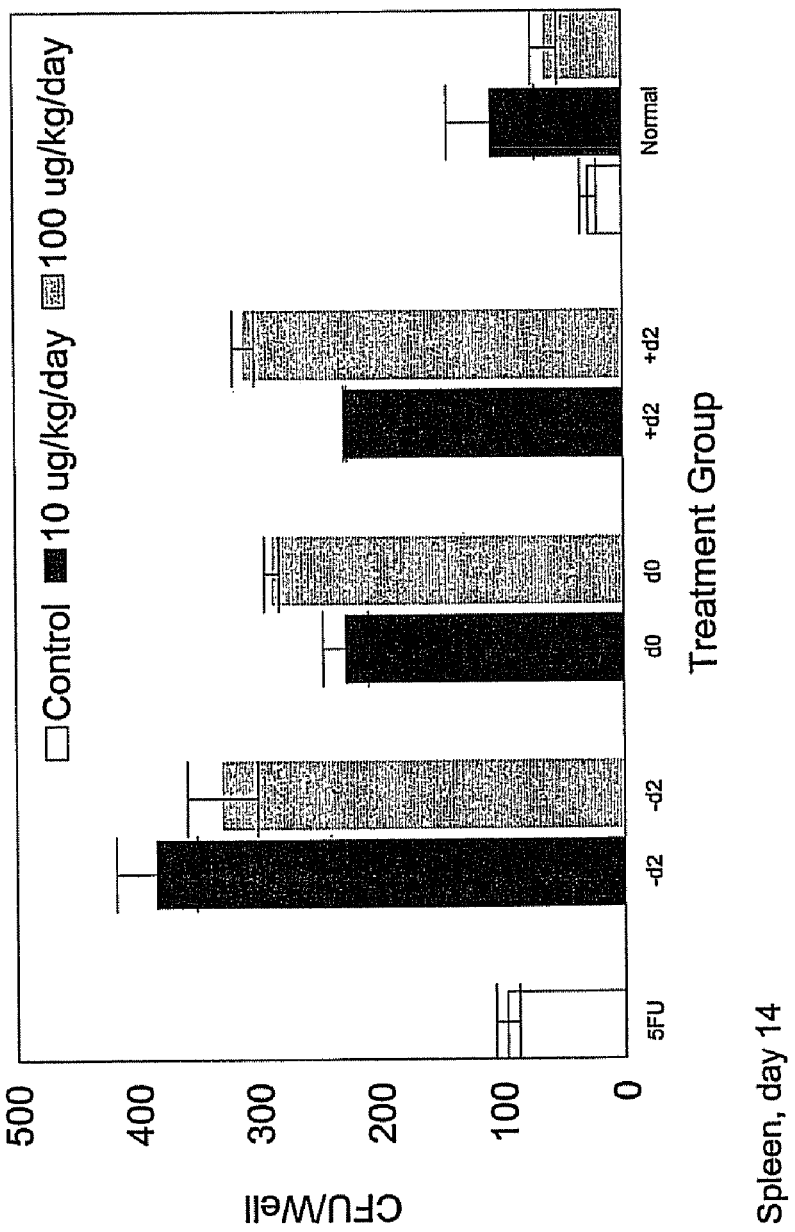
FIG. 15 is a graph showing the effect of AII treatment on CFU-GM cell number on day 7 after culture initiation following spleen harvest 14 days after 5FU treatment.
Figure 16:
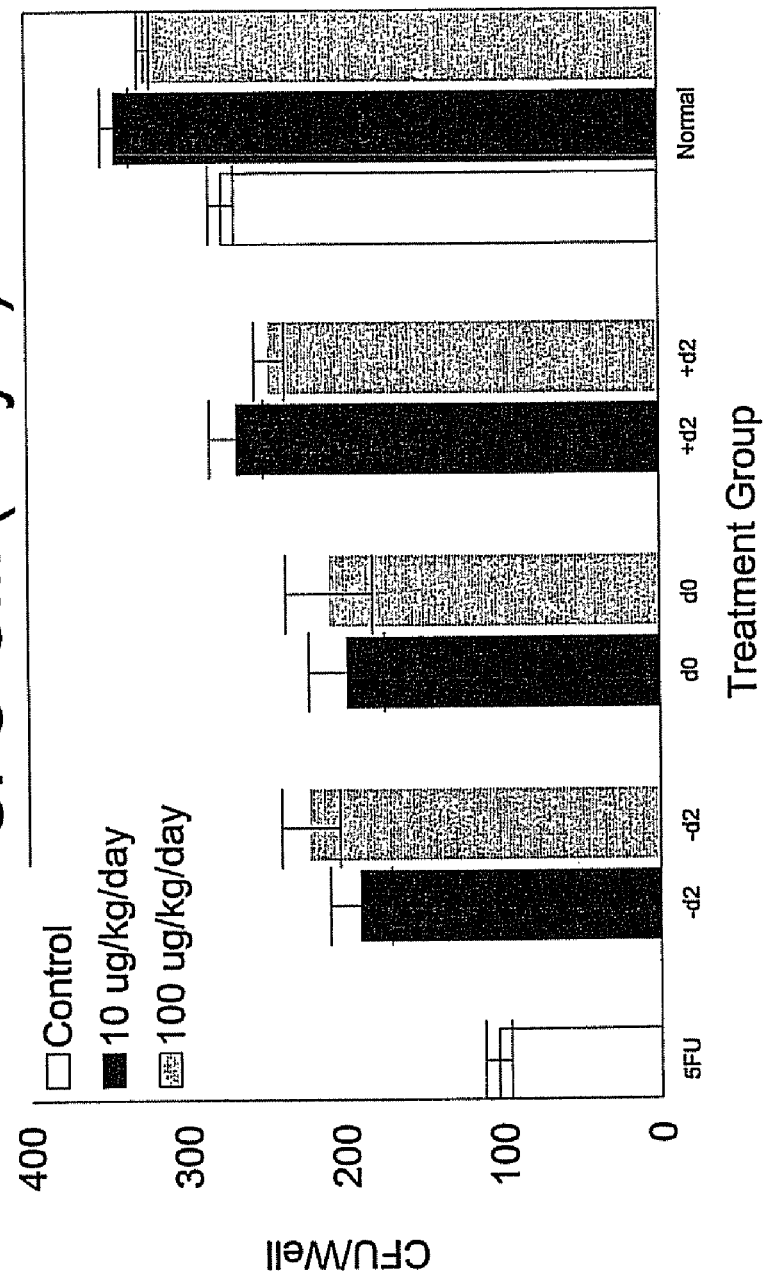
FIG. 16 is a graph showing the effect of AII treatment on CFU-GM cell number on day 7 after culture initiation following bone marrow harvest 7 days after 5FU treatment.
Figure 17:
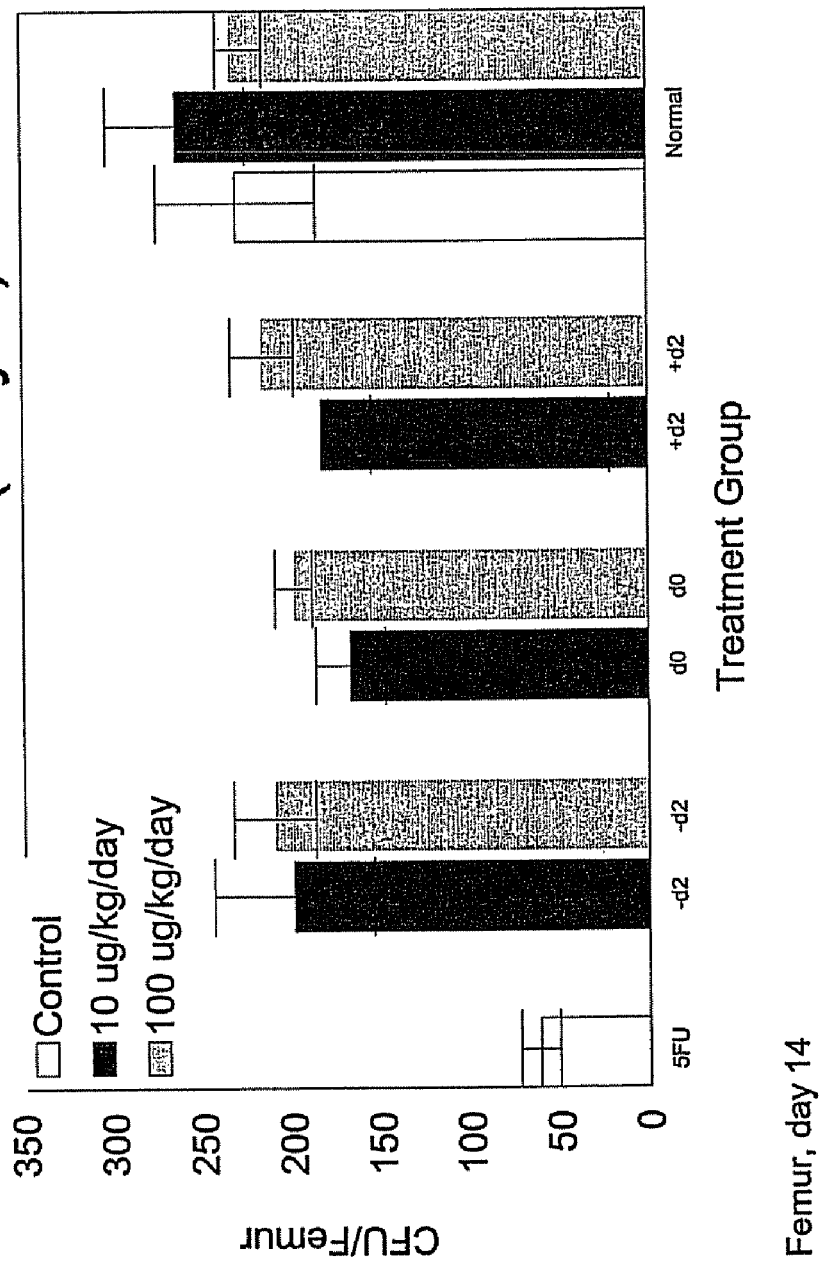
FIG. 17 is a graph showing the effect of AII treatment on CFU-GM cell number on day 7 after culture initiation following femur harvest 7 days after 5FU treatment.
Figure 18:
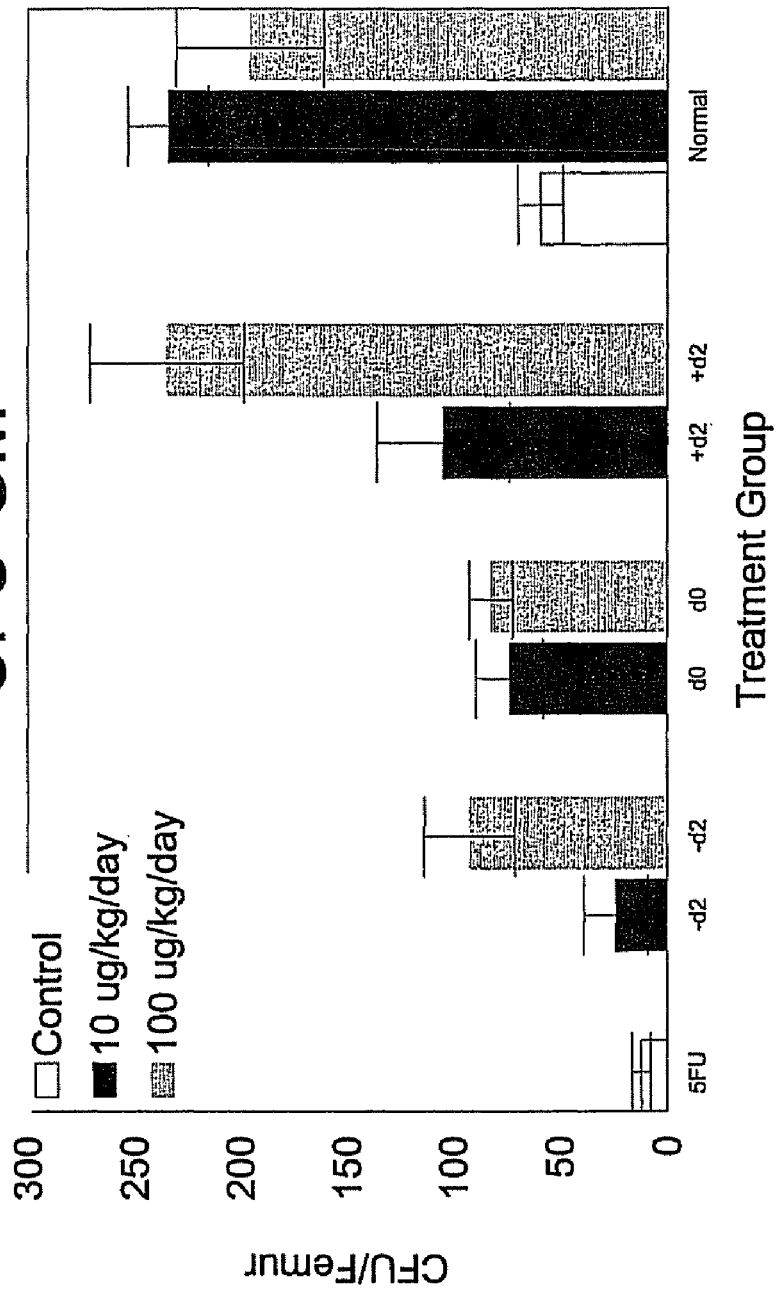
FIG. 18 is a graph showing the effect of AII treatment on CFU-GM cell number in the bone marrow on day 7 after 5FU treatment.
Figure 19:
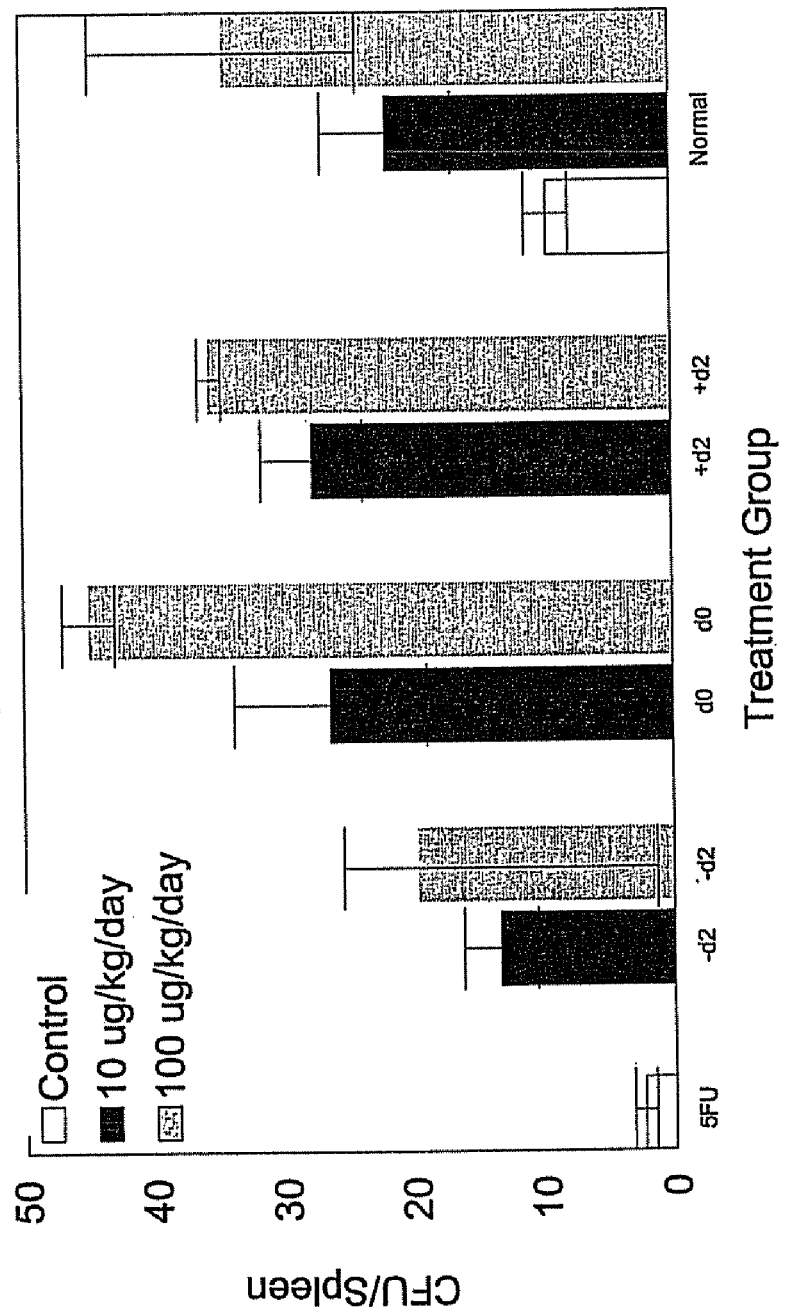
FIG. 19 is a graph showing the effect of AII treatment on CFU-GM cell number in the spleen on day 7 after 5FU treatment.
Figure 20:
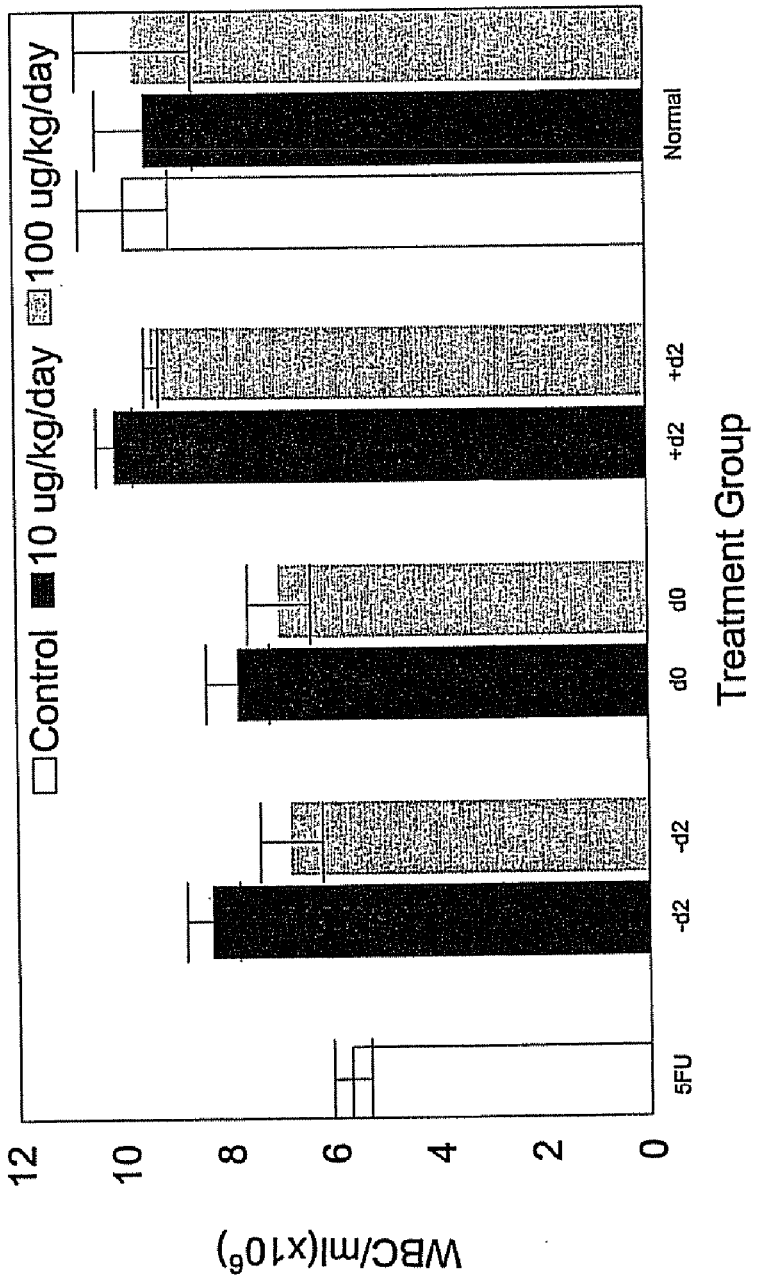
FIG. 20 is a graph showing the effect of AII treatment on white blood cell number in the blood on day 14 after 5FU treatment.
Figure 21:
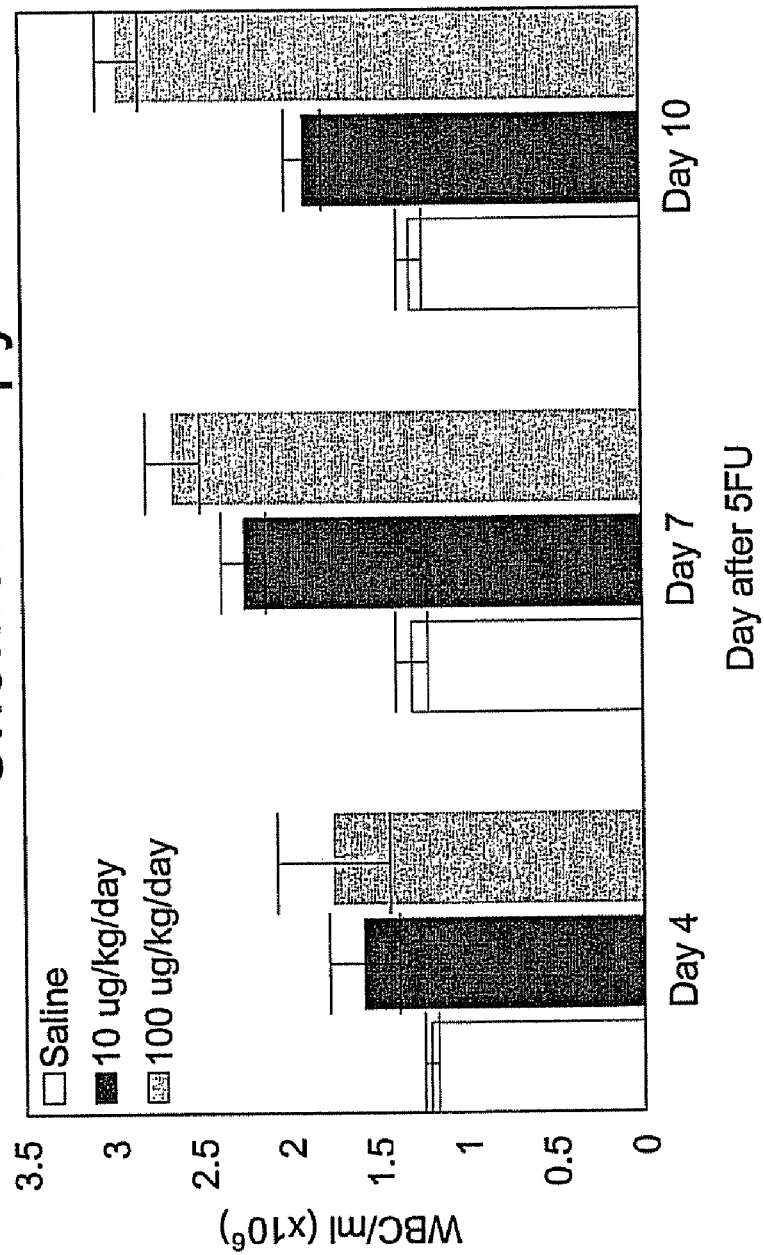
FIG. 21 is a graph of a different experiment showing the effect of AII treatment on white blood cell number in the blood on days 4, 7, and 10 after 5FU treatment.
Figure 22:
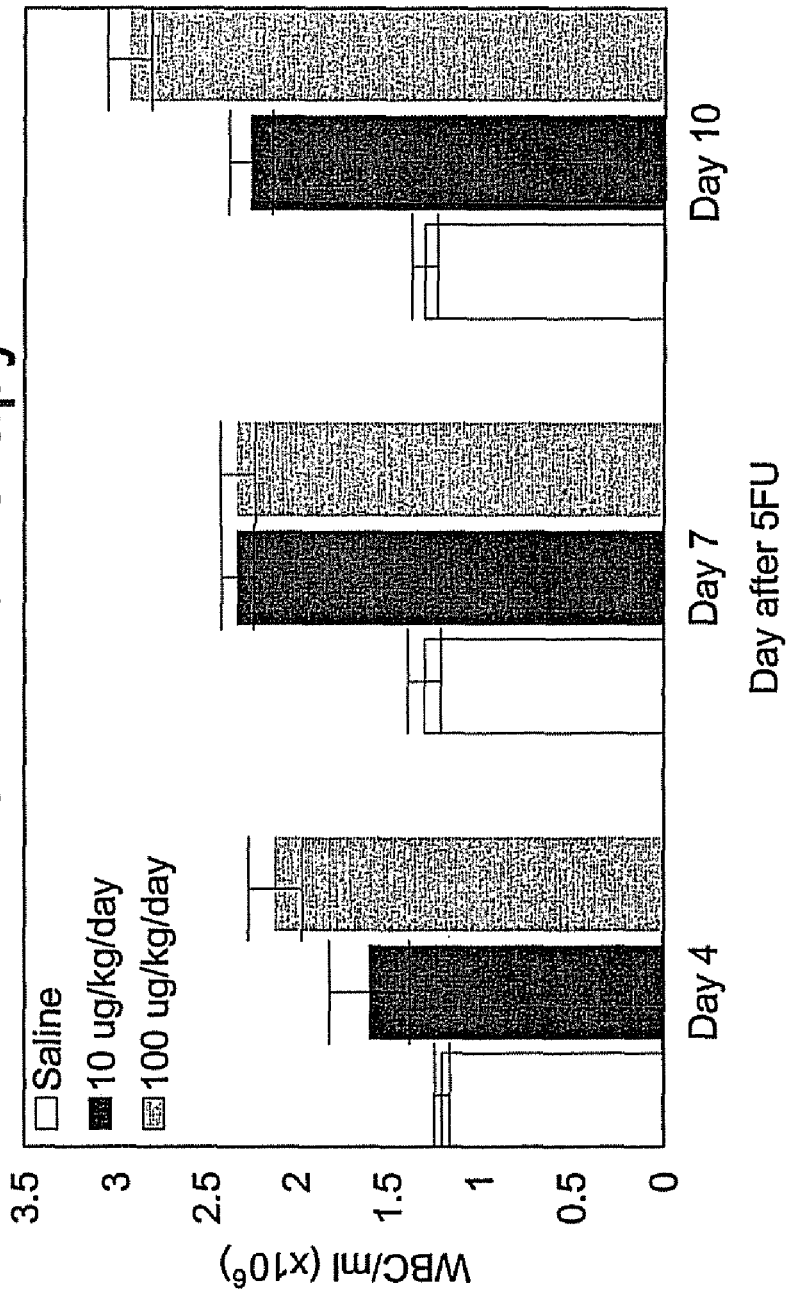
FIG. 22 is a graph showing the effect of AII(1-7) treatment on white blood cell number in the blood on day 14 after 5FU treatment.
Figure 23:
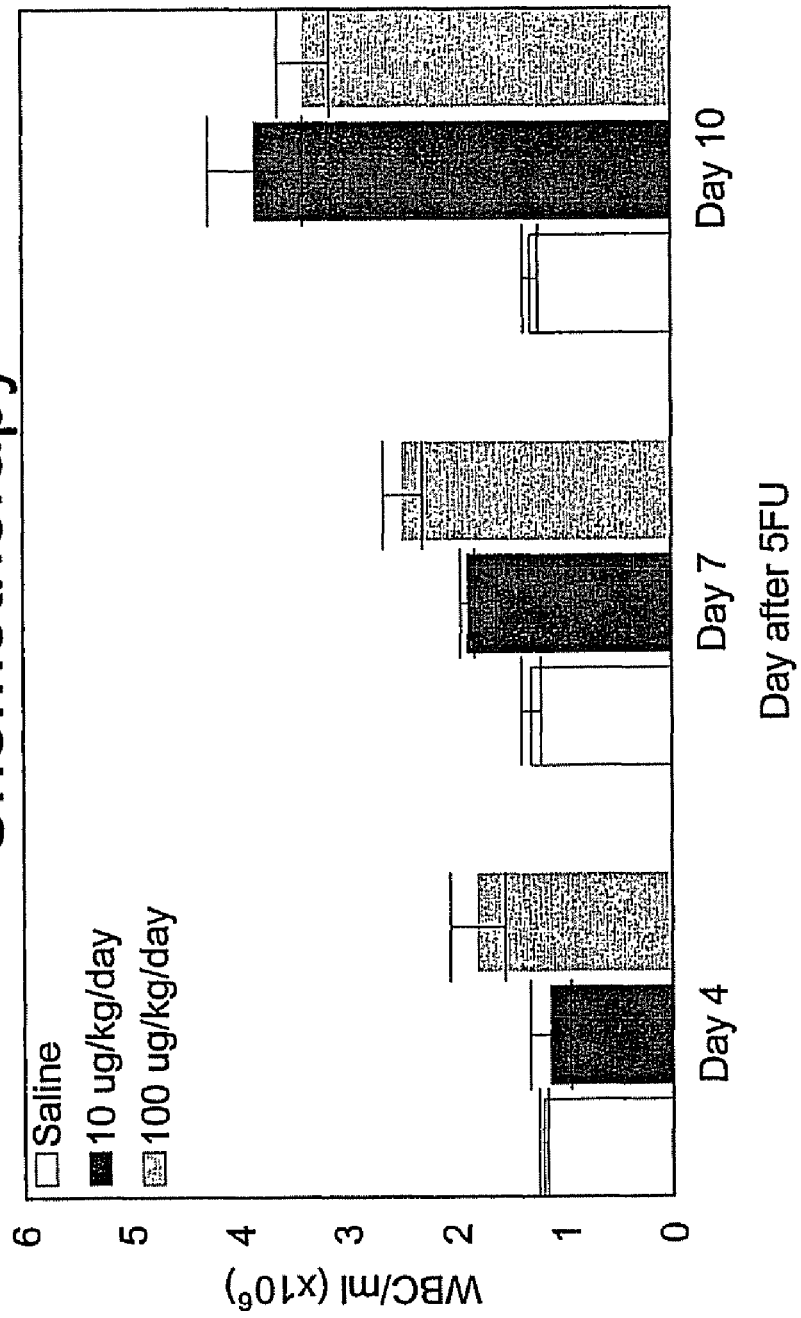
FIG. 23 is a graph showing the effect of 1GD treatment on white blood cell number in the blood on day 14 after 5FU treatment.
Figure 24:
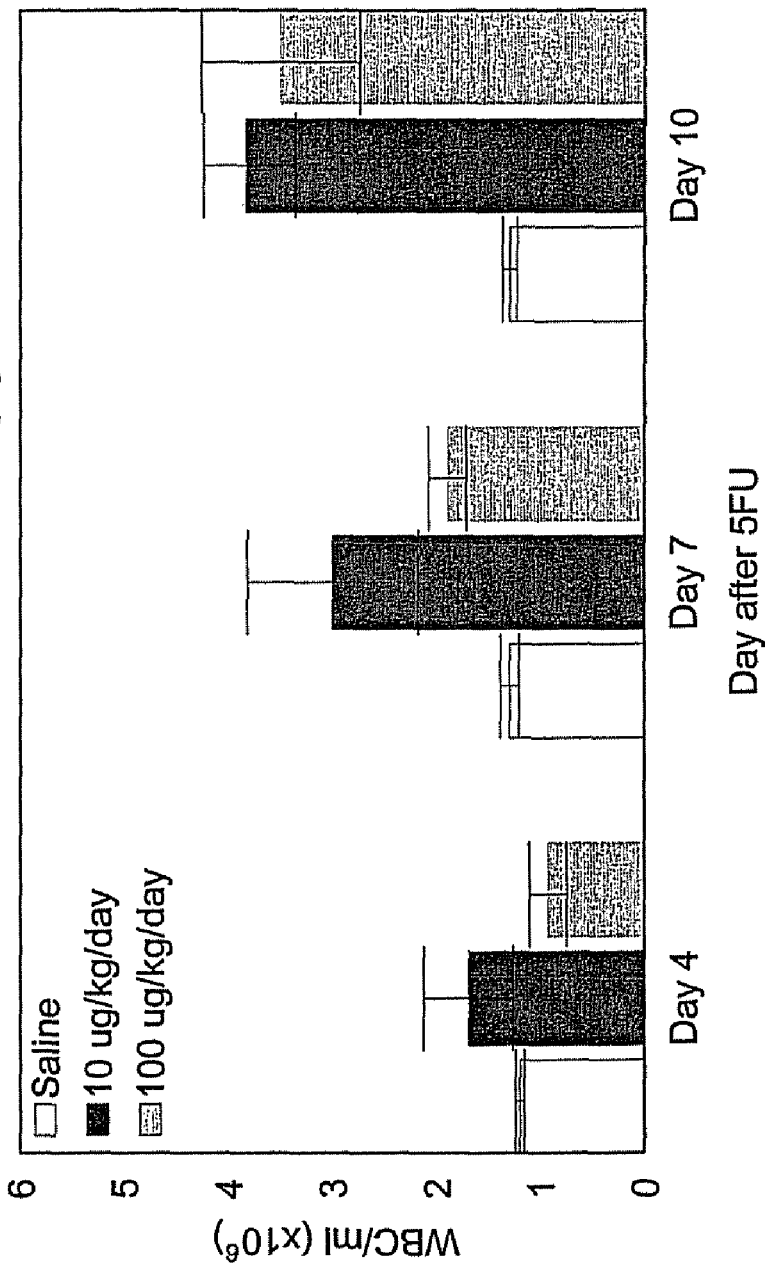
FIG. 24 is a graph showing the effect of 2GD treatment on white blood cell number in the blood on day 14 after 5FU treatment.
Figure 25:
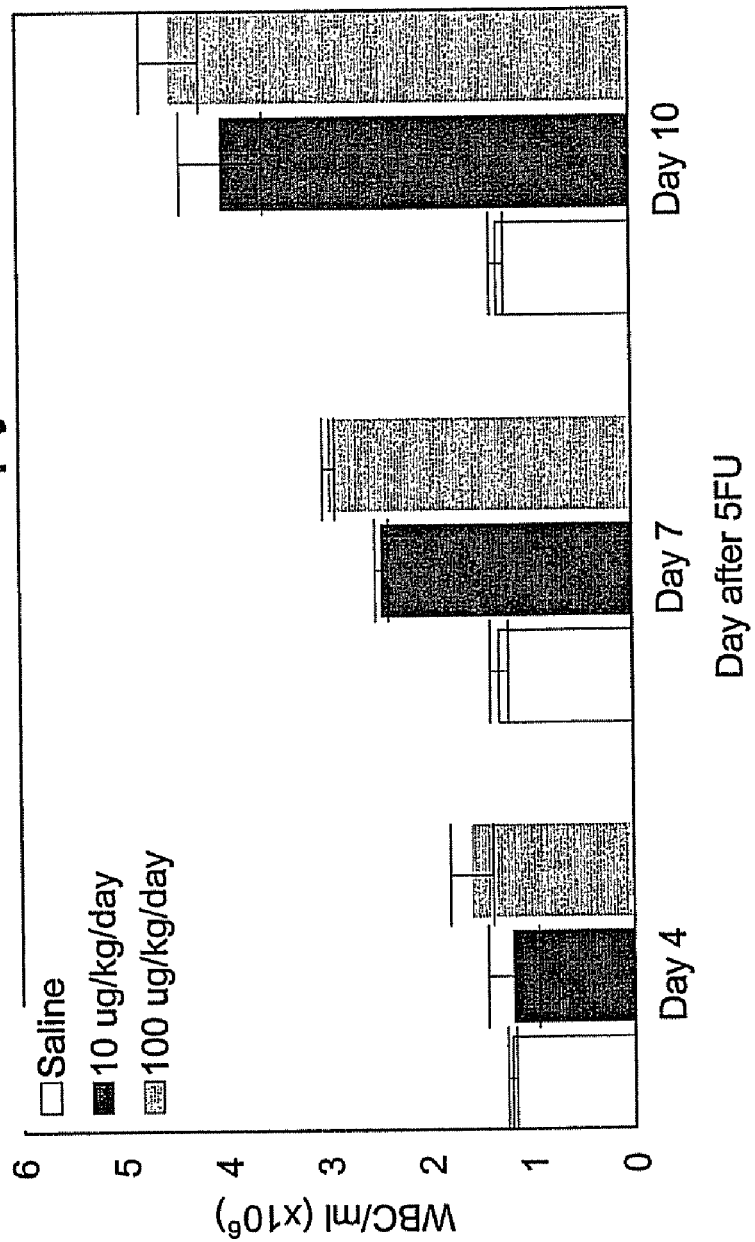
FIG. 25 is a graph showing the effect of 5GD treatment on white blood cell number in the blood on day 14 after 5FU treatment.
Figure 26:
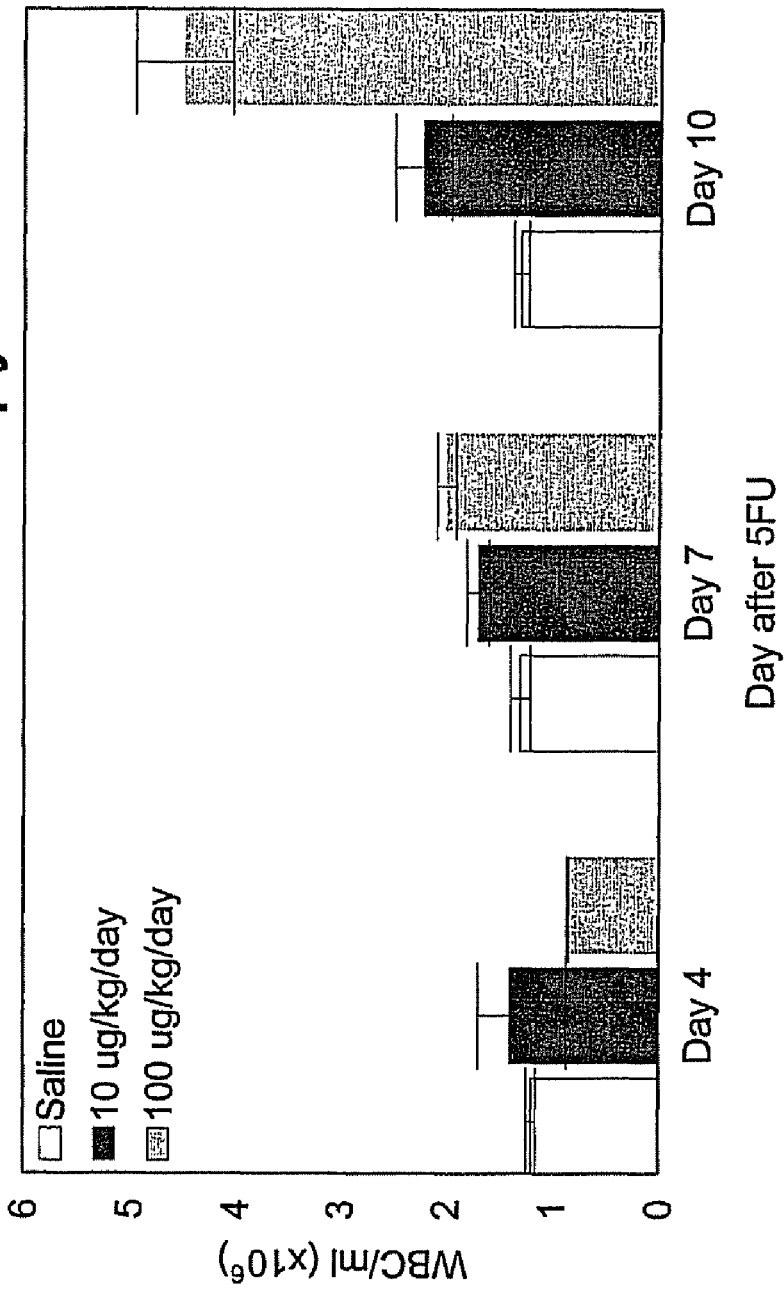
FIG. 26 is a graph showing the effect of 9GD treatment on white blood cell number in the blood on day 14 after 5FU treatment.
Figure 27:
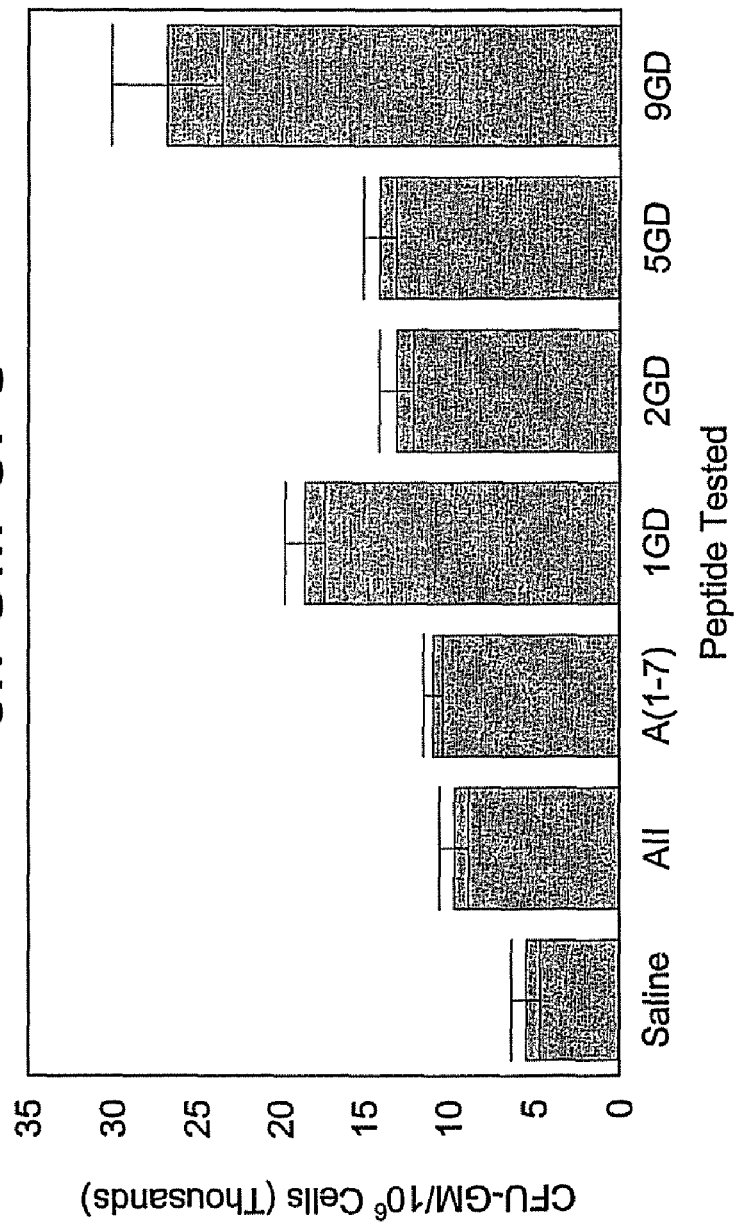
FIG. 27 is a graph showing the effect of 10 μg AII and AII analogues and fragments on GM-CFU numbers in the bone marrow on day 10 after 5FU treatment.
Figure 28:
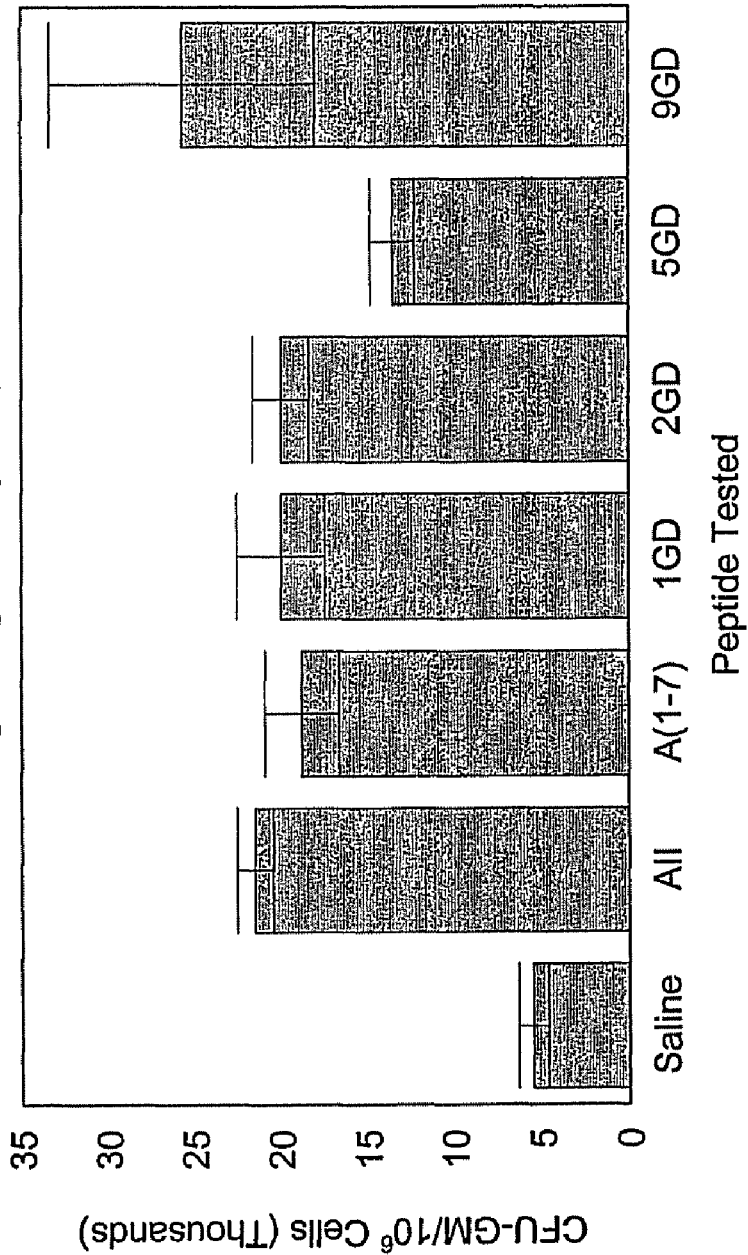
FIG. 28 is a graph showing the effect of 100 μg AII and AII analogues and fragments on GM-CFU numbers in the bone marrow on day 10 after 5FU treatment.
Figure 29:
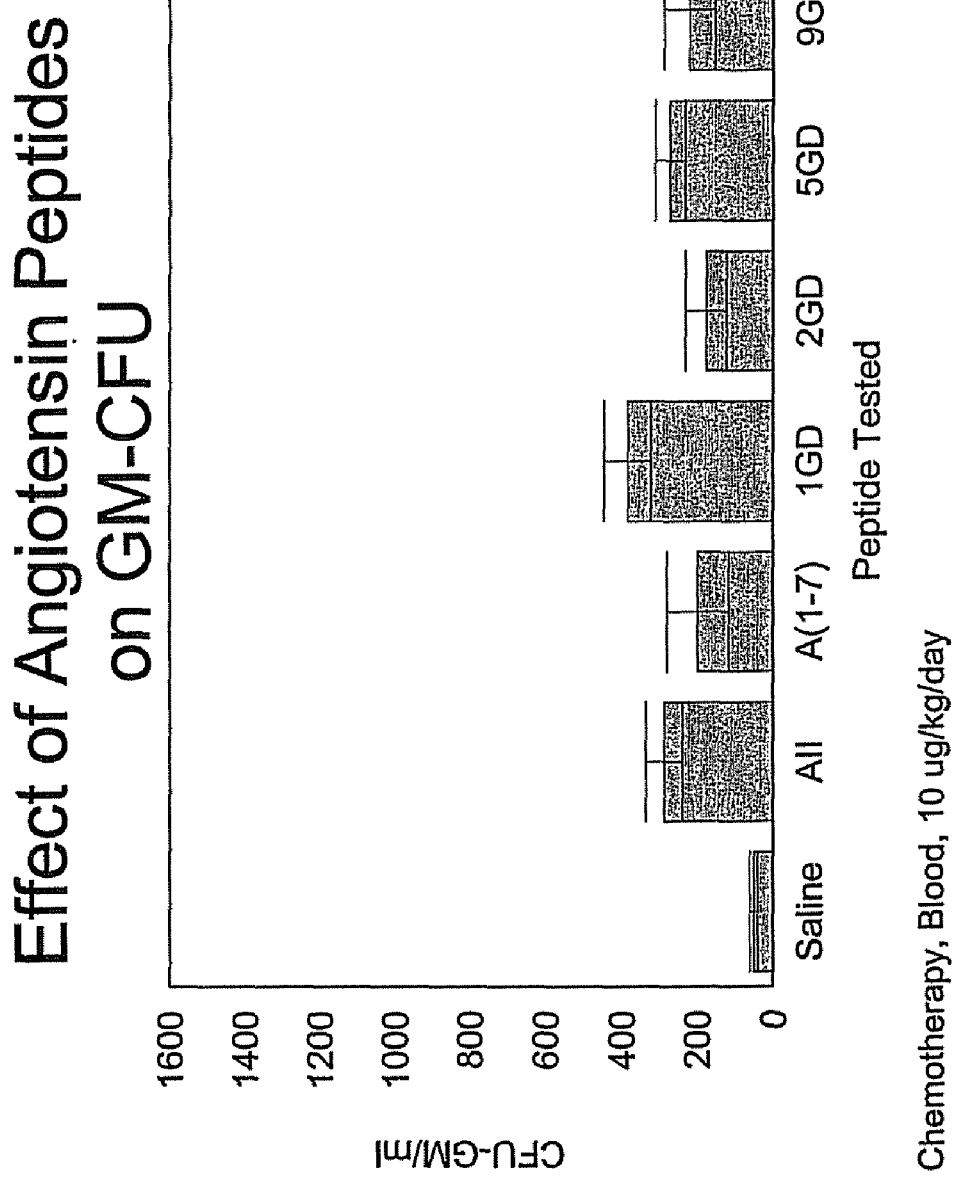
FIG. 29 is a graph showing the effect of 10 μg AII and AII analogues and fragments on GM-CFU numbers in the blood on day 10 after 5FU treatment.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods* and *Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As defined herein the phrase "hematopoietic cells" refers to undifferentiated hematopoietic stem cells, to committed hematopoietic progenitor cells, and to differentiated hematopoietic cells including, but not limited to megakaryocytes, platelets, red blood cells, monocytes, neutrophils, macrophages, and lymphocytes.

As defined herein, "chemotherapy side effects" encompass any deleterious effects suffered as a result of chemotherapy, including but not limited to hematopoietic toxicity, decreased mobilization of hematopoietic progenitor cells from bone marrow into the peripheral blood; anemia, myelosuppression, pancytopenia, thrombocytopenia, neutropenia, lymphopenia, leukopenia, stomatitis, alopecia, headache, and muscle pain.

Unless otherwise indicated, the term "angiotensin converting enzyme inhibitors" or "ACE inhibitors" includes any compound that inhibits the conversion of the decapeptide angiotensin I to angiotensin II, and include but are not limited to alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. (See for example Jackson, et al., Renin and Angiotensin in Goodman & Gilman's The Pharmacological Basis of Therapeutics, 9th ed., eds. Hardman, et al. (McGraw Hill, 1996); and U.S. Pat. No. 5,977,159.)

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount that is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (Clouston et al., *Genomics* 2:240-248 (1988); Kageyama et al, *Biochemistry* 23:3603-3609; Ohkubo et al., *Proc. Natl. Acad. Sci.* 80:2196-2200 (1983); each reference hereby incorporated in its entirety). The substance so formed is a decapeptide called angiotensin I (AI) which is converted to AII by the angiotensin converting enzyme (ACE) which removes the C-terminal His-Leu residues from AI [SEQ ID NO: 37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989; Berk et. al., *Hypertension* 13:305-14 (1989); Kawahara, et al., *BBRC* 150: 52-9 (1988); Naftilan, et al., *J. Clin. Invest.* 83:1419-23 (1989); Taubman et al., *J. Biol. Chem.* 264:526-530 (1989); Nakahara, et al., *BBRC* 184:811-8 (1992); Stouffer and Owens, *Circ. Res.* 70:820 (1992); Wolf, et al., *Am. J. Pathol.* 140:95-107 (1992); Bell and Madri, *Am. J. Pathol.* 137:7-12 (1990). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195:305-6 (1991).

We have previously demonstrated that angiotensinogen, angiotensin I (AI), AI analogues, AI fragments and analogues thereof, angiotensin II (AII), AII analogues, AII fragments or analogues thereof, and AII $AT_2$ type 2 receptor agonists are effective in accelerating wound healing and the proliferation of certain cell types, such as hematopoietic stem and lineage specific cells. See, for example, co-pending U.S. patent application Ser. No. 09/012,400, filed Jan. 23, 1998; 09/198,806 filed Nov. 24, 1998; 09/264,563, filed Mar. 8, 2000; 09/287, 674, filed Apr. 7, 1999; 09/255,136 filed Feb. 19, 1999; 09/245,680, filed Feb. 8, 1999; 09/250,703 filed Feb. 15, 1999; 09/246,525 filed Feb. 8, 1999; 09/266,293 Mar. 11, 1999; 09/332,582 filed Jun. 14, 1999; 09/373,962 filed Aug. 13, 1999; and 09/352,191 filed Jul. 12, 1999; as well as U.S. Pat. Ser. Nos. 5,015,629; 5,629,292; 5,716,935; 5,834,432; and 5,955,430; 6,096,709; 6,110,895.

Angiotensin II and its sarcosine analogue have also been used in combination with cytotoxic drugs to induce hypertension in humans and experimental animals undergoing intraarterial and intraperitoneal chemotherapy. (Taniguchi et al., J. Nuclear Medicine 37:1522-1523 (1996); Morita et al., Am. J. Clin. Oncol. 15:188-193 (1992); Ohigashi et al., Hepato-Gastroenterology 43:338-345 (1996); Cancer Chemother. Pharmacol. 39:113-121 (1996); Kuroiwa et al., Cancer Chemother. Pharmacol. 35:357-363 (1995); Li et al., Br. J. Cancer 67:975-980 (1993); Dworkin et al., Br. J. Cancer 76:1205-1210 (1997); Sato et al., World J. Surg. 19:836-842 (1995); Mutoh et al., Urol. Int. 48:175-180 (1992). In each of these cases, the use of angiotensin II was intended to selectively increase blood flow to the tumor vasculature relative to normal vasculature, thereby increasing the delivery of cytotoxic agent to the tumor. None of these studies demonstrated or suggested that the use of angiotensin II or its sarcosine analogue would be effective in increasing hematopoietic cell survival, hematopoietic stem cell mobilization into peripheral blood following chemotherapy, or the reduction in chemotherapy side effects.

Based on all of the above, it would be unexpected that the use of angiotensinogen, angiotensin I (AI), AI analogues, AI fragments and analogues thereof, AII, AII analogues, AII fragments or analogues thereof, AII $AT_2$ type 2 receptor agonists, or ACE inhibitors would be effective in increasing hematopoietic cell survival following chemotherapy, for reducing or preventing other side effects of chemotherapy, such as anemia, and for mobilizing hematopoietic progenitor cells from bone marrow into peripheral blood.

A peptide agonist selective for the AT2 receptor (AII has 100 times higher affinity for AT2 than AT1) has been identified. This peptide is p-aminophenylalanine 6-AII ["(p-$NH_2$-Phe)-6-AII)"], Asp-Arg-Val-Tyr-Ile-Xaa-Pro-Phe [SEQ ID NO. 36] wherein Xaa is p-$NH_2$-Phe (Speth and Kim, BBRC 169:997-1006 (1990). This peptide gave binding characteristics comparable to AT2 antagonists in the experimental models tested (Catalioto, et al., *Eur. J. Pharmacol.* 256:93-97 (1994); Bryson, et al., *Eur. J. Pharmacol.* 225:119-127 (1992).

The effects of AII receptor and AII receptor antagonists have been examined in two experimental models of vascular injury and repair which suggest that both AII receptor subtypes (AT1 and AT2) play a role in wound healing (Janiak et al., *Hypertension* 20:737-45 (1992); Prescott, et al., *Am. J. Pathol.* 139:1291-1296 (1991); Kauffman, et al., *Life Sci.* 49:223-228 (1991); Viswanathan, et al., *Peptides* 13:783-786 (1992); Kimura, et al., *BBRC* 187:1083-1090 (1992).

Many studies have focused upon AII(1-7) (AII residues 1-7) or other fragments of AII to evaluate their activity. AII (1-7) elicits some, but not the full range of effects elicited by AII. Pfeilschifter, et al., *Eur. J. Pharmacol.* 225:57-62 (1992); Jaiswal, et al., *Hypertension* 19(Supp. II):II-49-II-55 (1992); Edwards and Stack, *J. Pharmacol. Exper. Ther.* 266:506-510 (1993); Jaiswal, et al., *J. Pharmacol. Exper. Ther.* 265:664-673 (1991); Jaiswal, et al., *Hypertension* 17:1115-1120 (1991); Portsi, et al., Br. *J. Pharmacol.* 111:652-654 (1994).

Other data suggests that the AII fragment AII(1-7) acts through a receptor(s) that is distinct from the AT1 and AT2 receptors which modulate AII activity. (Ferrario et al., *J. Am. Soc. Nephrol.* 9:1716-1722 (1998); Iyer et al., Hypertension 31:699-705 (1998); Freeman et al., Hypertension 28:104 (1996); Ambuhl et al., Brain Res. Bull. 35:289 (1994)). Thus, AII(1-7) activity on a particular cell type cannot be predicted based solely on the effect of AII on the same cell type. In fact, there is some evidence that AII(1-7) often opposes the actions of AII. (See, for example, Ferrario et al., Hypertension 30:535-541 (1997))

As hereinafter defined, a preferred class of AT2 agonists for use in accordance with the present invention comprises angiotensinogen, angiotensin I (AI), AI analogues, AI fragments and analogues thereof, AII, AII analogues, AII fragments or analogues thereof or AII $AT_2$ type 2 receptor agonists having p-NH-Phe in a position corresponding to a position 6 of AII. In addition to peptide agents, various non-peptidic agents (e.g., peptidomimetics) having the requisite AT2 agonist activity are further contemplated for use in accordance with the present invention, as well as compounds fused to the active agent to provide some further desired property.

The active AII analogues, fragments of AII and analogues thereof of particular interest in accordance with the present invention comprise a sequence of at least three contiguous amino acids of groups $R^1$-$R^8$ in the sequence of general formula I $R^1$-$R^2$-$R^3$-$R^4$-$R^5$-$R^6$-$R^7$-$R^8$ wherein $R^1$ is selected from Asp, Glu, Asn, Acpc (1-aminocyclopentane carboxylic acid), Ala, Me$^2$Gly, Pro, Bet, Glu(NH$_2$), Gly, Asp(NH$_2$) and Suc, $R^2$ is selected from Arg, Lys, Ala, Orn, Ser(Ac), Sar, D-Arg and D-Lys;

$R^3$ is selected from the group consisting of Val, Ala, Leu, Lys, norLeu, Ile, Gly, Pro, Aib, Acpc and Tyr;

$R^4$ is selected from the group consisting of Tyr, Tyr(PO$_3$)$_2$, Thr, Ser, Ala, homoSer and azaTyr;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

Particularly preferred combinations for $R^1$ and $R^2$ are Asp-Arg, Asp-Lys, Glu-Arg and Glu-Lys.

In alternate embodiments, the active agents comprise a sequence of at least four, five, six, seven, or eight contiguous amino acids of groups $R^1$-$R^8$ in the sequence of general formula I. In a further alternative, the active agents consist essentially of a sequence of at least four, five, six, seven, or eight contiguous amino acids of groups $R^1$-$R^8$ in the sequence of general formula I.

Compounds falling within the category of AT2 agonists useful in the practice of the invention include the All analogues set forth above subject to the restriction that $R^6$ is p-NH$_2$-Phe. In a further preferred embodiment of all of the aspects of the invention, the active agent comprises a sequence selected from the group consisting of angiotensinogen, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO: 34; SEQ ID NO:35, SEQ ID NO:36, SEQ ID NO:37, SEQ ID NO:38, SEQ ID NO:39, SEQ ID NO:40, and SEQ ID NO:41.

Particularly preferred embodiments of this class comprise the following sequences: AII (SEQ ID NO:1), AIII or AII(2-8), Arg-Val-Tyr-Ile-His-Pro-Phe [SEQ ID NO:2]; AII(3-8), also known as des1-AIII or AIV, Val-Tyr-Ile-His-Pro-Phe [SEQ ID NO:3]; AII(1-7), Asp-Arg-Val-Tyr-Ile-His-Pro {SEQ ID NO:4]; AII(2-7). Arg-Val-Tyr-Ile-His-Pro [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ ID NO:9]; AII(1-4), Asp-Arg-Val-Tyr [SEQ ID NO:10]; and AII(1-3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(6-8), His-Pro-Phe [SEQ ID NO:14] and AII (4-8), Tyr-Ile-His-Pro-Phe [SEQ ID NO:15] were also tested and found not to be effective.

In a particularly preferred embodiment, the active agents of the present invention comprise an amino acid sequence of the following general formula:

Asp-Arg-R1-R2-Ile-His-Pro-R3, wherein

R1 is selected from the group consisting of Val, Pro, Lys, Norleu, and Leu;

R2 is selected from the group consisting of Ala, Tyr, and Tyr(PO$_3$)$_2$; and

R3 is Phe or is absent.

In a most particularly preferred embodiment, the active agent comprises a sequence selected from the group consisting of SEQ ID NO:1, SEQ ID NO:4, SEQ ID NO:31, SEQ ID NO:32, SEQ ID NO:33, SEQ ID NO:38, SEQ ID NO:39, SEQ ID NO:40, and SEQ ID NO:41.

Another class of compounds of particular interest in accordance with the present invention are those comprising a sequence of the general formula II $R^2$-$R^3$-$R^4$-$R^5$-$R^6$-$R^7$-$R^8$ in which $R^2$ is selected from the group consisting of H, Arg, Lys, Ala, Orn, Ser(Ac), Sar, D-Arg and D-Lys;

$R^3$ is selected from the group consisting of Val, Ala, Leu, norLeu, Lys, Ile, Gly, Pro, Aib, Acpc and Tyr;

$R^4$ is selected from the group consisting of Tyr, Tyr(PO$_3$)$_2$, Thr, Ser, Ala homoSer and azaTyr;

$R^5$ is selected from the group consisting of Ile, Ala, Leu, norLeu, Val and Gly;

$R^6$ is selected from the group consisting of His, Arg or 6-NH$_2$-Phe;

$R^7$ is selected from the group consisting of Pro or Ala; and $R^8$ is selected from the group consisting of Phe, Phe(Br), Ile and Tyr.

A particularly preferred subclass of the compounds of general formula II has the formula

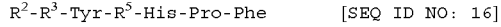

```
R²-R³-Tyr-R⁵-His-Pro-Phe        [SEQ ID NO: 16]
``` wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4-8) was ineffective in repeated tests; this is believed to be due to the exposed tyrosine on the N-terminus.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |

It has been suggested that AII and its analogues adopt either a gamma or a beta turn (Regoli, et al., *Pharmacological Reviews* 26:69 (1974)). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Val, Ala, Leu, norLeu, Ile, Gly, Pro, Aib, Acpc and Tyr. Lys has also been found to be effective at position $R^3$.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr (PO$_3$)$_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). Ala has also been found to be effective at position $R^4$.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, Gly and Val.

In the angiotensinogen, AI, AI analogues, AI fragments and analogues thereof, AII analogues, fragments and analogues of fragments of particular interest in accordance with the present invention, $R^6$ is His, Arg or 6-NH$_2$-Phe. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro in order to provide the most desirable orientation of $R^8$. In position $R^8$, both a hydrophobic ring and an anionic carboxyl terminal appear to be particularly useful in binding of the analogues of interest to receptors; therefore, Tyr and especially Phe are preferred for purposes of the present invention.

Analogues of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |

TABLE 2-continued

Angiotensin II Analogues

| Analogue Name | Amino Acid Sequence | All Analogue Sequence Identifier |
|---|---|---|
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be produced by any standard method, including but not limited to recombinant DNA technology and conventional synthetic methods including, but not limited to, those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. Alternatively, the active agents can be prepared by standard recombinant DNA techniques.

In one aspect, the present invention provides methods and kits for increasing hematopoietic cell survival following chemotherapy, and treating and preventing the adverse effects of chemotherapy, comprising the administration of angiotensinogen, angiotensin I (AI), AI analogues, AI fragments and analogues thereof, angiotensin II (AII), AII analogues, AII fragments or analogues thereof or AII AT$_2$ type 2 receptor agonists (hereinafter referred to as "active agents") to a patient undergoing chemotherapy.

In another aspect, the present invention provides methods and kits for mobilizing hematopoietic progenitor cells from bone marrow into peripheral blood comprising the administration of the active agents of the invention to a patient in need of such treatment. This aspect of the invention can also be used to treat a patient in need of chemotherapy.

The methods of the invention are appropriate for use with chemotherapy using any cytotoxic agent, including, but not limited to, cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound which is capable of destroying proliferating cells. For a general discussion of cytotoxic agents used in chemotherapy, see Sathe, M. et al., Cancer Chemotherapeutic Agents: Handbook of Clinical Data (1978), hereby incorporated by reference.

The methods of the invention are also particularly suitable for those patients in need of repeated or high doses of chemotherapy. For some cancer patients, hematopoietic toxicity frequently limits the opportunity for chemotherapy dose escalation. Repeated or high dose cycles of chemotherapy may be responsible for severe stem cell depletion leading to severe long-term hematopoietic sequelea and marrow exhaustion. The methods of the present invention provide for improved mortality and blood cell count when used in conjunction with chemotherapy.

The active agents may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques, or intraperitoneally.

The active agents may be made up in a solid form (including granules, powders or suppositories) or in a liquid form (e.g., solutions, suspensions, or emulsions). The compounds of the invention may be applied in a variety of solutions. Suitable solutions for use in accordance with the invention are sterile, dissolve sufficient amounts of the peptide, and are not harmful for the proposed application. In this regard, the compounds of the present invention are very stable but are hydrolyzed by strong acids and bases. The compounds of the present invention are soluble in organic solvents and in aqueous solutions at pH 5-8.

The active agents may be subjected to conventional pharmaceutical operations such as sterilization and/or may contain conventional adjuvants, such as preservatives, stabilizers, wetting agents, emulsifiers, buffers etc.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Formulations suitable for topical administration include liquid or semi-liquid preparations suitable for penetration through the skin (e.g., liniments, lotions, ointments, creams, or pastes) and drops suitable for administration to the eye, ear, or nose.

The dosage regimen of active agents for the methods of the invention is based on a variety of factors, including the type of injury, the age, weight, sex, medical condition of the individual, the severity of the condition, the route of administration, and the particular compound employed. Dosage levels of the order of between 0.1 ng/kg and 10 mg/kg body weight of the active agents per body weight are useful for all methods of use disclosed herein.

In all of these embodiments, the compounds of the invention can be administered prior to, simultaneously with, or subsequent to chemotherapeutic exposure.

In a preferred embodiment, the active agent is administered subcutaneously. A suitable subcutaneous dose of the active agent is preferably between about 0.1 ng/kg and about 10 mg/kg administered twice daily for a time sufficient to increase white blood cell survival after chemotherapy treatment or to mobilize hematopoietic progenitor cells from bone marrow into peripheral blood. In a more preferred embodiment, the concentration of active agent is between about 100 ng/kg body weight and about 10.0 mg/kg body weight. In a most preferred embodiment, the concentration of active agent is between about 2.5 µg/kg body weight and about 100 µg/kg body weight. This dosage regimen maximizes the therapeutic benefits of the subject invention while minimizing the amount of agonist needed. Such an application minimizes costs as well as possible deleterious side effects. For example, the active agents are administered to an oncology patient for up to 30 days prior to a course of chemotherapy and for up to 60 days post-chemotherapy. The therapy is administered for 1 to 6 times per day at dosages as described above. In a further preferred embodiment, the active agent is administered once per day.

For subcutaneous administration, the active ingredient may comprise from 0.0001% to 10% w/w, e.g., from 1% to 2% by weight of the formulation, although it may comprise as much as 10% w/w, but preferably not more than 5% w/w, and more preferably from 0.1% to 1% of the formulation.

In a preferred embodiment, subcutaneous administration of between about 1 to 1000 µg/kg/day of the active agents is initiated at between one week before to one week after administration of a chemotherapeutic agent. In a most preferred embodiment, administration of the active agents begins either at the time chemotherapy is initiated, or 0-10 days after initiation.

In another preferred embodiment of the invention, a subject undergoes repeated cycles of treatment according to the method of this invention. Preferably, a subsequent treatment cycle commences only after administration of the compounds of the invention has terminated, and the subject's blood cell counts (e.g., white blood cell count, as well as platelet and megakaryocyte count) have returned to a therapeutically acceptable level (as determined by the attending veterinarian or physician), permitting the repeated chemotherapy.

In a further aspect, the present invention provides kits for increasing hematopoietic cell survival following chemotherapy, reducing the incidence and/or severity of anemia and other side effects of chemotherapy, and/or mobilizing hematopoietic progenitor cells from bone marrow into peripheral blood, wherein the kits comprise an effective amount of the active agents for increasing hematopoietic cell survival following chemotherapy, reducing chemotherapy-induced side effects, or for mobilizing hematopoietic progenitor cells from bone marrow into peripheral blood, and instructions for using the amount effective of active agent as a therapeutic. In a preferred embodiment, the kit further comprises a pharmaceutically acceptable carrier, such as those adjuvants described above. In another preferred embodiment, the kit further comprises a means for delivery of the active agent to a patient. Such devices include, but are not limited to, syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery may either contain the effective amount of the active agents, or may be separate from the compounds, which are then applied to the means for delivery at the time of use.

In a further embodiment, the present invention provides an article of manufacture, comprising the pharmaceutical composition of the invention preloaded into a syringe or other delivery system, for home use by patients undergoing chemotherapy.

In another aspect, the present invention provides a pharmaceutical composition, comprising an amount effective of the active agents to increase hematopoietic cell survival and/or to reduce the side effects of chemotherapy in a chemotherapy patient, and a pharmaceutically acceptable carrier. In a preferred embodiment, the active agent is AII(1-7), and the effective dosage is between about 2.5 µg/kg/day and 100 µg/kg/day.

In a further embodiment, the pharmaceutical composition further comprises an amount of cytokine effective for increasing the production of hematopoietic cells. According to this aspect of the invention, cytokines appropriate for use include, but are not limited to, granulocyte colony stimulating factor (G-CSF), granulocyte-macrophage-CSF (GM-CSF), epidermal growth factor (EGF), interleukin 11, erythropoietin, thrombopoietin, megakaryocyte development and growth factor, pixykines, stem cell factor, FLT-ligand, as well as interleukins 1, 3, 6, and 7. In a most preferred embodiment, the cytokine is granulocyte colony stimulating factor.

The methods, kits, and pharmaceutical compositions of the present invention, significantly enhance the utility of presently available treatments for clinical chemotherapeutic treatments, by providing improved methods for increasing hematopoietic blood cell survival following chemotherapy, reducing the side effects of chemotherapy, and mobilizing hematopoietic progenitor cells from bone marrow into peripheral blood, and also by their cytokine sparing effect, in that significantly reduced amounts of cytokines are needed when administered with the active agents to a patient undergoing chemotherapy.

The present invention may be better understood with reference to the accompanying example that is intended for purposes of illustration only and should not be construed to limit the scope of the invention, as defined by the claims appended hereto.

Example 1

Effect of AII on White Blood Cell Mobilization and Recovery after 5 Fluorouracil Treatment This study was designed to test the effect of AII on the recovery of white blood cells in lymphoid organs and on the level of granulocyte macrophage precursors (CFU-GM) in the blood (ie: mobilization), spleen (mobilization), and bone marrow (recovery) after intravenous administration of 5-fluorouracil (5FU).

Subcutaneous administration of AII (either 10 or 100 μg/kg/day) was initiated either two days before (−d2), the day of (d0), or two days after (d2) intravenous administration of 5FU. On either day 7 or 14 after 5FU administration, the animals were necropsied and the spleen, thymus, peripheral blood, and bone marrow were harvested. The number of white blood cells in each of the lymphoid organs, or the number of CFU-GM present in all the organs except the thymus, were then assessed. The number of white blood cells per lymphoid organ was assessed after (1) dissociation of the tissues into a single cell suspension (thymus and spleen), (2) flushing of bone marrow from the femur, or (3) lysis of red blood cells by a hypotonic ammonium chloride solution (blood). An aliquot of the cell suspension was diluted with 0.04% trypan blue and the number of cells was determined by microscopic analysis using a hematocytometer. After counting, the number of cells were adjusted to allow a 1:10 dilution of cells into semi-solid medium containing fetal bovine serum, bovine serum albumin, methyl cellulose, stem cell factor, interleukin 3, interleukin 6, L-glutamine, 2 mercaptoethanol, human transferrin and bovine insulin. On day 7 after culture initiation, the number of CFU-GM per well (and then per organ) was determined by microscopic analysis (FIGS. 1-20). These data demonstrate that AII treatment after chemotherapy leads to significantly enhanced white blood cell mobilization and/or recovery in all of the tissues tested.

Example 2

Effect of AII Analogues and Fragments on White Blood Cell Mobilization and Recovery after 5-Fluorouracil Treatment The method was conducted as described above in Example 1, except that mice were injected subcutaneously with 150 mg/kg body weight of 5FU, and AII peptide analogues and fragments were tested. Administration of the peptides (see Table 3) was begun 2 days after and continued until 10 days after 5FU administration, at which time the mice were euthenized for evaluation of bone marrow and blood GM-CFU progenitors. On days 4 and 7 after 5FU administration, blood was taken under anesthesia from the retro-orbital sinus. On day 10, blood was taken by cardiac puncture.

The data for these experiments is shown in FIGS. 21-30, and demonstrate that all peptides tested accelerated the recovery of white blood cells after chemotherapy (FIGS. 21-26), increased the number of GM-CFU progenitors in the bone marrow (FIGS. 27-28), and increased the mobilization of GM-CFU progenitors from the bone marrow into the peripheral blood (FIGS. 29-30), relative to controls. The peptides were effective at both concentrations tested (10 μg/kg/day and 100 μg/kg/day), and the efficacy generally increased with increasing length of treatment.

TABLE 3

| Designation for Analogues/Fragments | | | |
|---|---|---|---|
| Name | Abbreviation | Sequence | SEQ ID NO: |
| 1GD | Ala4-AII(1-7) | DRVAIHP | SEQ ID NO: 38 |
| 2GD | Pro3-AII(1-7) | DRPYIHP | SEQ ID NO: 39 |
| 5GD | Lys3-AII(1-7) | DRKYIHP | SEQ ID NO: 40 |
| 9GD | NorLeu-AII(1-7) | DR(nor)YIHP | SEQ ID NO: 41 |
| AII(1-7) | | DRVYIHP-- | SEQ ID NO: 4 |
| AII | | DRVYIHPF | SEQ ID NO. 1 |

Example 3

Effect of AII(1-7) on Hematopoietic Recovery After Cytoxan

In this study, female C57B1/6 mice were injected with 200 mg/kg cyclophosphamide ("cytoxan") intravenously. Administration of AII(1-7) by subcutaneous injection was begun 2 days before or 2 days after administration of the antineoplastic and continued daily until necropsy for evaluation of mature formed blood elements in the circulation and the number of GM-CFU in the bone marrow and peripheral blood. On days 5, 9, 14, 21 and 28 after cytoxan administration, blood was taken under metofane anesthesia from the retro-orbital sinus to assess white blood cell (WBC) and platelet number.

Figure 31A:
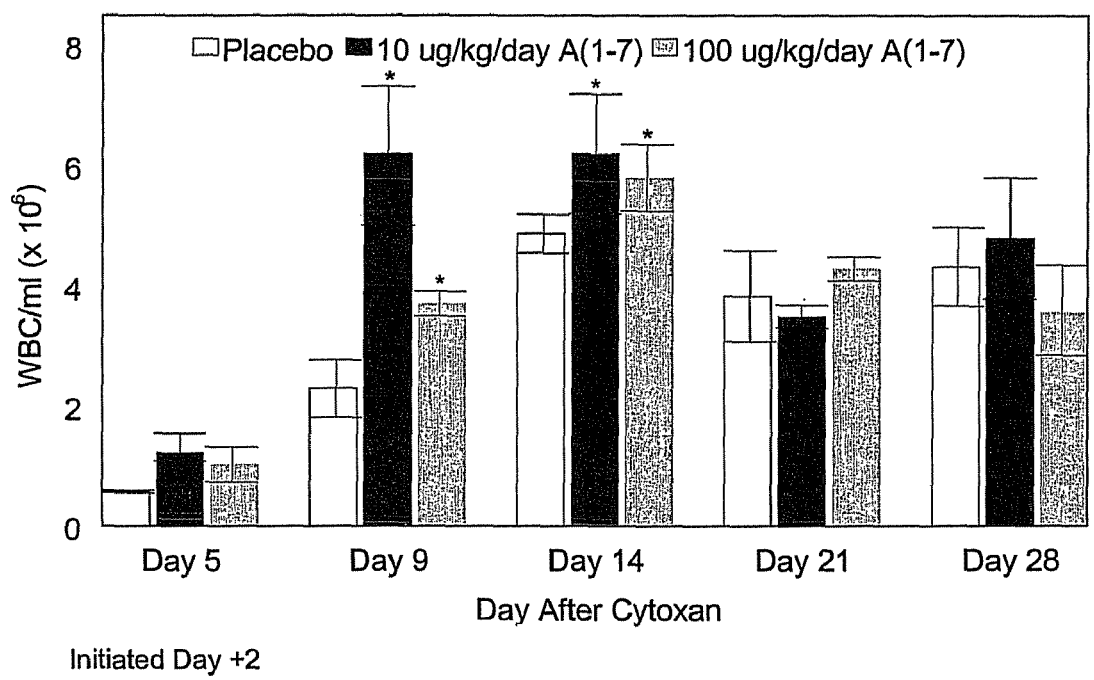
FIGS. 31a and b. Female C57B1/6 mice, 6-8 weeks old, were treated with 200 mg/kg cytoxan by intravenous injection. Two days after (panel a) and two days before (panel b) cytoxan injection, subcutaneous administration of AII(1-7) was initiated. Various times after cytoxan injection, the animals were necropsied and peripheral blood harvested. The number of white blood cells was counted by hematocytometer after red blood cell lysis. An asterisk indicates a result significantly different from saline control ($p \leq 0.05$). These data are mean and standard error of 4 animals per group (dose and time point).
Figure 31B:
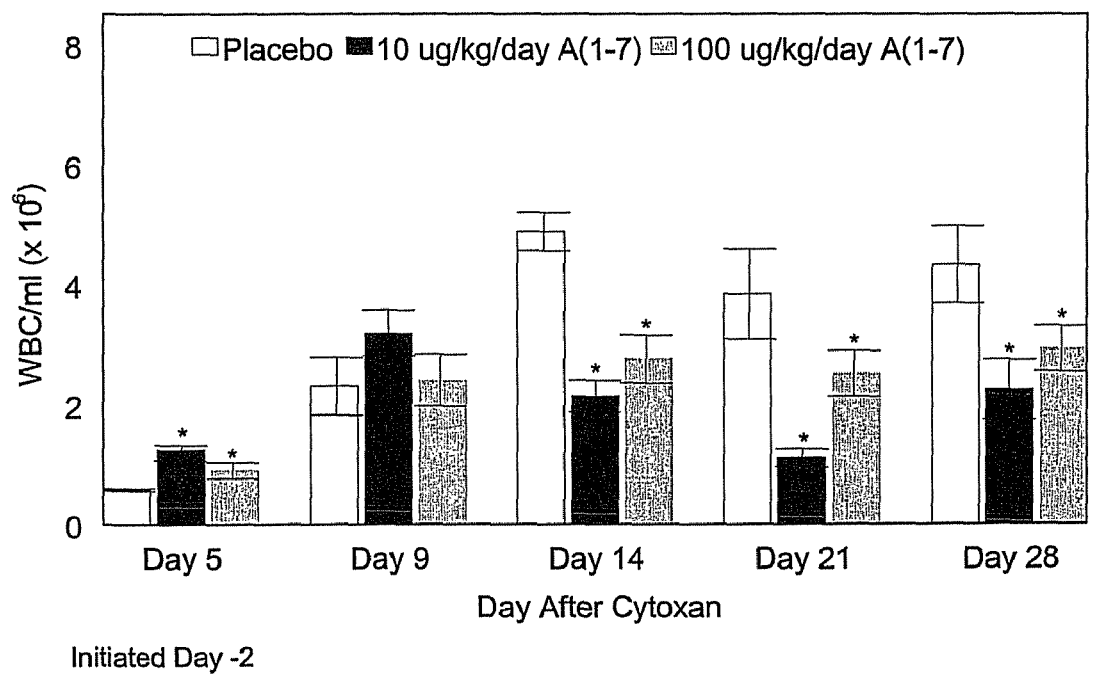

The data showed that AII(1-7) accelerated the recovery of WBC after intravenous administration of cyclophosphamide when treatment with peptides was initiated two days after the chemotherapeutic (FIG. 31a). The increase in WBC number was observed within 9 days after cyclophosphamide treatment. However, if AII(1-7) treatment was initiated two days prior to the administration of cyclophosphamide, there was a decrease in WBC number compared with control starting on day 14 after exposure to the chemotherapeutic (FIG. 31b).

Figure 32A:
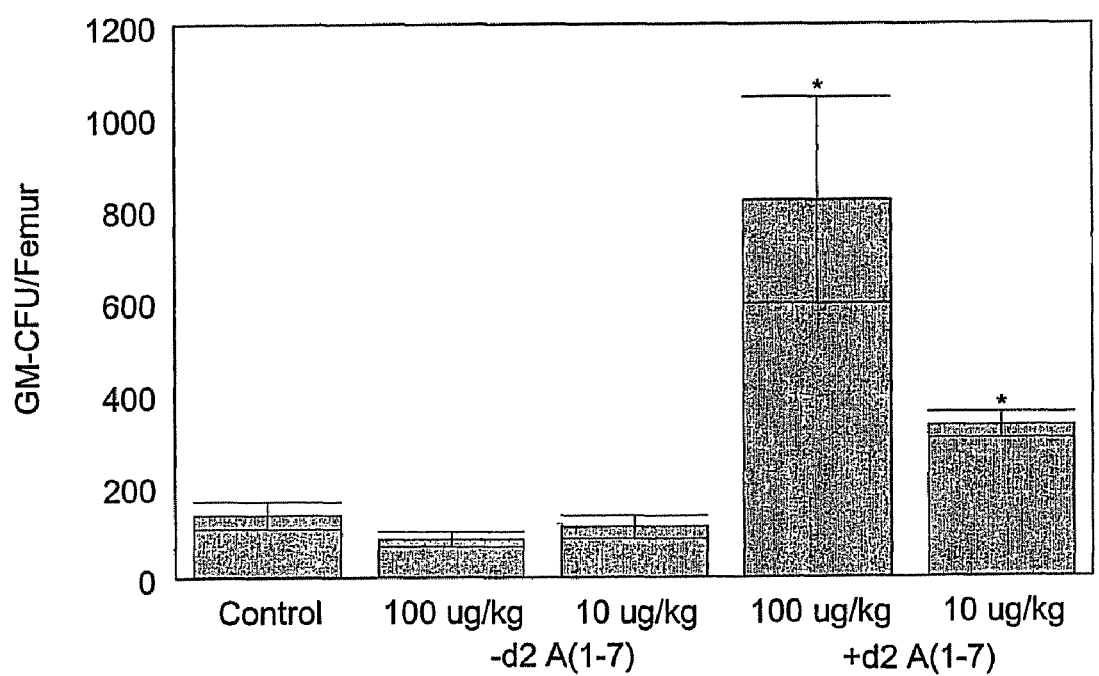
FIGS. 32a and b. Female C57B1/6 mice, 6-8 weeks old, were treated with 200 mg/kg cytoxan by intravenous injection. Two days after and two days before cytoxan injection, subcutaneous administration of AII(1-7) was initiated. Twenty eight after cytoxan injection, the animals were necropsied and bone marrow (panel a) or peripheral blood (panel b) harvested. The number of GM-CFU formed from cells isolated from bone marrow or peripheral blood after red blood cell lysis by culturing in semi solid medium containing recombinant colony stimulating factors was counted. An asterisk indicates a result significantly different from saline control ($p \leq 0.05$). These data are mean and standard error of 3 animals per group (dose and time point).
Figure 32B:
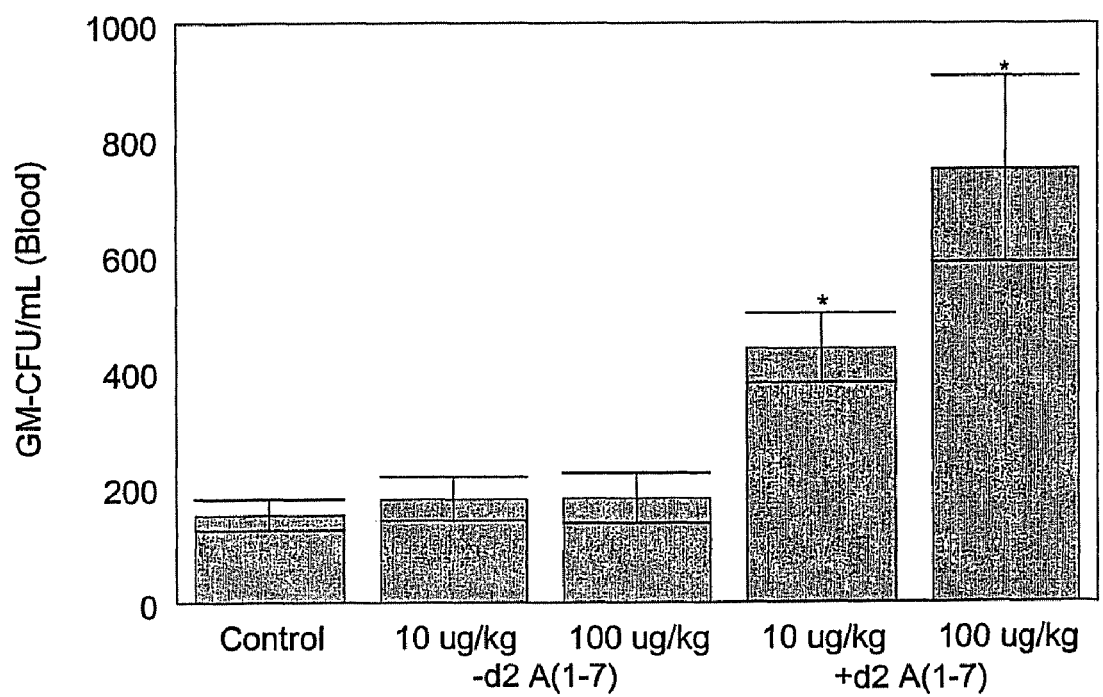

Administration of cyclophosphamide also significantly reduced the number of myeloid progenitors (GM-CFU) in the bone marrow. Treatment with AII(1-7) (100 μg/kg/day) 2 days prior to treatment with cytoxan slightly reduced the number of GM-CFU in the bone marrow of treated animals (FIG. 32a). However, initiation of AII(1-7) administration 2 days after chemotherapy increased the number of myeloid progenitor cells in the bone marrow (FIG. 32a). Further, administration of AII(1-7), initiated after cyclophosphamide treatment, increased the number of myeloid progenitors in the peripheral blood (FIG. 32b).

Example 4

Effect of Angiotensin Fragments and Ace Inhibitor on Recovery After Chemotherapy The next study was designed to test the effect of angiotensin peptides and the angiotensin converting enzyme inhibitor, enalapril on recovery of white blood cells, platelets and hemoglobin after chemotherapy, as well as on granulocyte-macrophage colony forming units (GM-CFU) in the blood and bone marrow.

Female C67B1/6 mice (4 per group), 6-8 weeks old, were injected with 150 mg/kg 5FU intravenously. Administration of the peptides (AII (100 μg/kg/day), AII(1-7) (10 or 100 μg/kg/day), AII(1-5) (10 or 100 μg/kg/day), and AII(1-6) (100 μg/kg/day)), by subcutaneous injection, or enalapril (30 mg/kg/day) by oral gavage, was begun 2 days after administration of the antineoplastic and continued daily until 28 days after 5FU administration, at which time the mice were euthanized for evaluation of white blood cell numbers, platelets, hemoglobin levels and the number of GM-CFU in the bone marrow and peripheral blood. On days 7, 10, 14 and 21 after 5FU administration, blood was taken under anesthesia from the retro-orbital sinus to assess white blood cell number, platelet number, and hemoglobin levels.

Retro-Orbital Bleeding of Mice

The mice were bled from the retro-orbital sinus at days 7, 10, 14 and 21. The mice were anesthetized with Metofane (an inhaled anesthesia). Approximately 150-200 µl of blood were obtained from the retro-orbital sinus with a heparinzed capillary tube. The blood was then placed in a 1.7 ml microfuge tube containing 10 mM EDTA and held on ice until further processing.

Hemoglobin Assay

One hundred µl of blood was pipetted into a centrifuge tube, to which 900 µl of distilled water was added. The blood and water were mixed by inversion and allowed incubate at 4° C. for 20 minutes. The tube was then centrifuged at 12000 rpm to precipitate the cellular debris for 20 to 30 minutes at room temperature. Twenty µl of the supernatant from this centrifugation was then added into triplicate wells of a 96 well plate containing 180 µl of distilled water. The optical density was then read using a microplate reader at 570 nM.

WBC and Platelet Evaluation

Twenty µl of blood was mixed with 200 µl of red blood cell (RBC) lysing solution (0.83% $NH_4Cl$, 10 mM EDTA, 0.5% $NaHCO_3$). The mixture was then incubated for 10 minutes at 4° C. After this incubation, the supernatant was removed and the pellet was resuspended in 100 µl of PBS. To this, 100 µl of 0.04% trypan blue was added. This mixture was vortexed and the number of WBC (baseline was approximately $10^7$ cells/ml) was evaluated by hematocytometer under light microscopy and the number of platelets (baseline was approximately $2.5 \times 10^8$ platelets/ml) was evaluated by hematocytometer under phase contrast microscopy.

Evaluation of GM-CFU Progenitors in the Blood and Bone Marrow

The blood was harvested by cardiac puncture on day 10 to assess mobilization of myeloid progenitors into the peripheral blood. The femurs and tibia were also collected and the bone marrow was harvested by flushing with PBS containing 2% fetal calf serum. After collection of the blood and bone marrow, the red blood cells were lysed with a hypotonic solution (described above), mixed with 0.04% trypan blue, and the number of nucleated cells assessed by hematocytometer under light microscopy. Aliquots of cells were then resuspended at $1 \times 10^5$ cells/ml (bone marrow) or $1 \times 10^6$ cells/ml (blood). One hundred µl of each suspension was added to 900 µl of semisolid medium containing 0.9% methyl cellulose in Iscove's MDM, 15% fetal calf serum, 1% bovine serum albumin, 10 µg/ml bovine pancreatic insulin, 200 µg/ml human transferrin, $10^{-4}$ M 2-mercaptoethanol, 2 mM glutamine, 10 ng/ml recombinant murine interleukin 3, 10 ng/ml recombinant human interleukin 6, 50 ng/ml recombinant murine stem cell factor and 3 units/ml erythropoietin. This mixture was then added to duplicate wells of a 24 well plate. The cultures were then placed at 37° C. in a humidified atmosphere of 5% $CO_2$ in air. At day 14, the number of myeloid colonies formed was enumerated under phase contrast microscopy.

Results

These studies were conducted to compare the effect of angiotensin fragments on hematopoietic recovery after chemotherapy. No animals were lost to analysis as a result of these therapies. The animals that died succumbed to anesthesia during the bleeding procedures.

There was no difference in baseline white blood cell (WBC) number between groups (8.6 to $9.0 \times 10^6$ per ml). Baseline platelet numbers ranged from 2.4 to $2.6 \times 10^8$ platelets per ml. No differences were observed between the groups at baseline.

Figure 33:
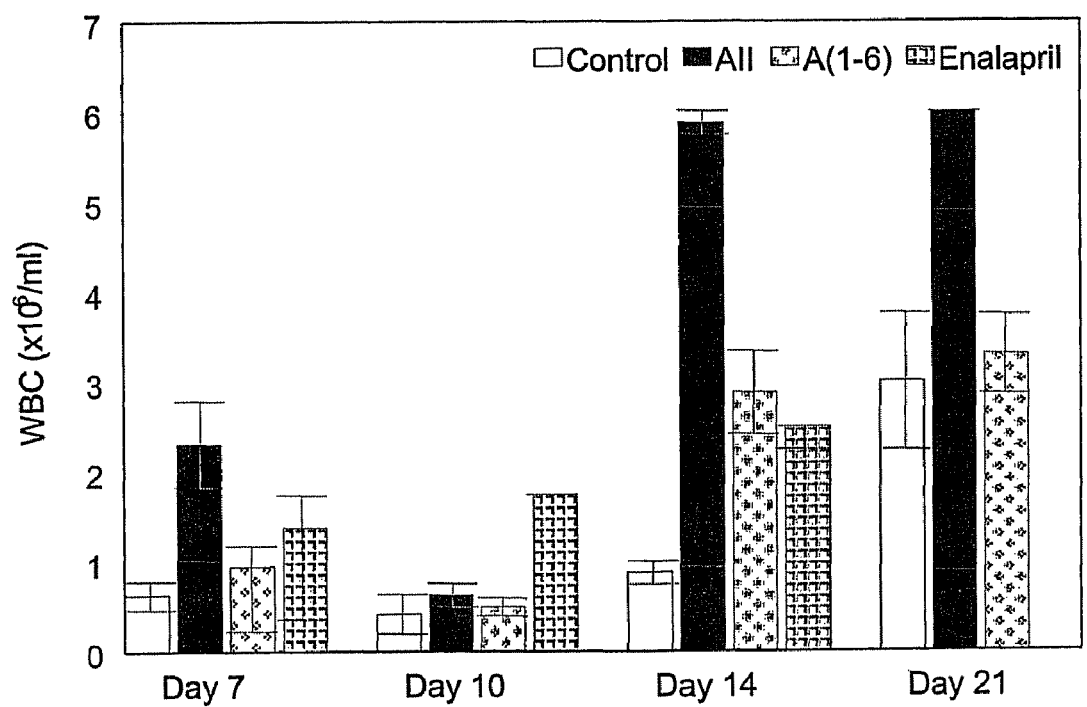
FIG. 33. Effect of AII analogues and enalapril on the increase in white blood cells in the peripheral blood after intravenous administration of 5FU.
Figure 34:
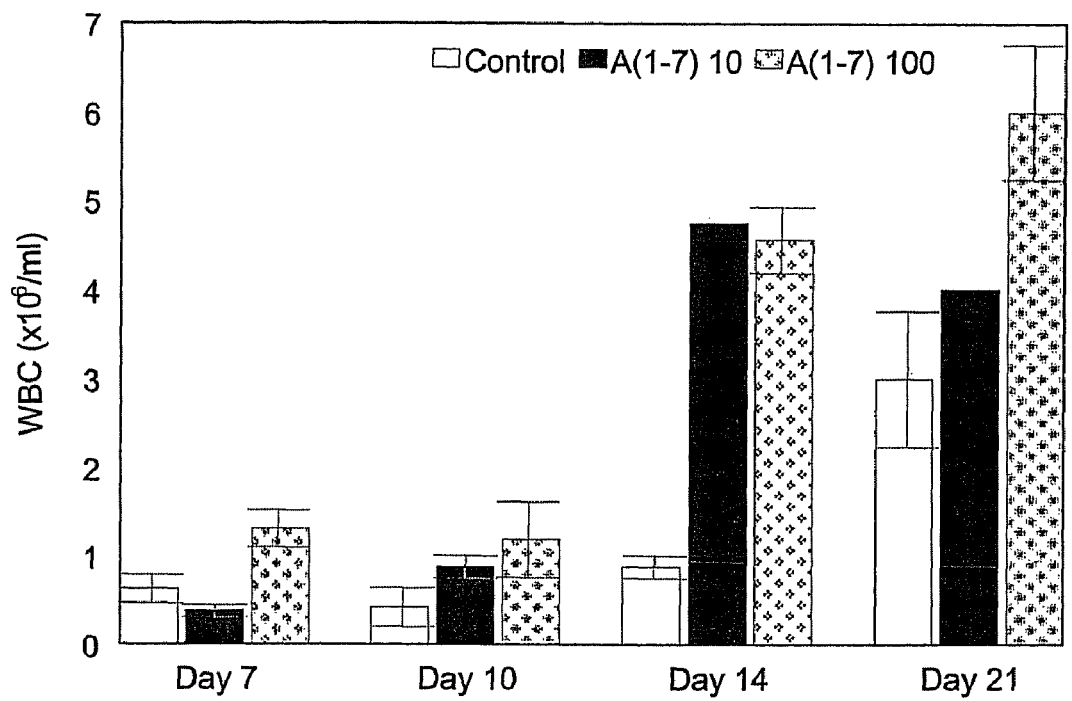
FIG. 34. Effect of AII analogues and enalapril on the increase in white blood cells in the peripheral blood after intravenous administration of 5FU.
Figure 35:
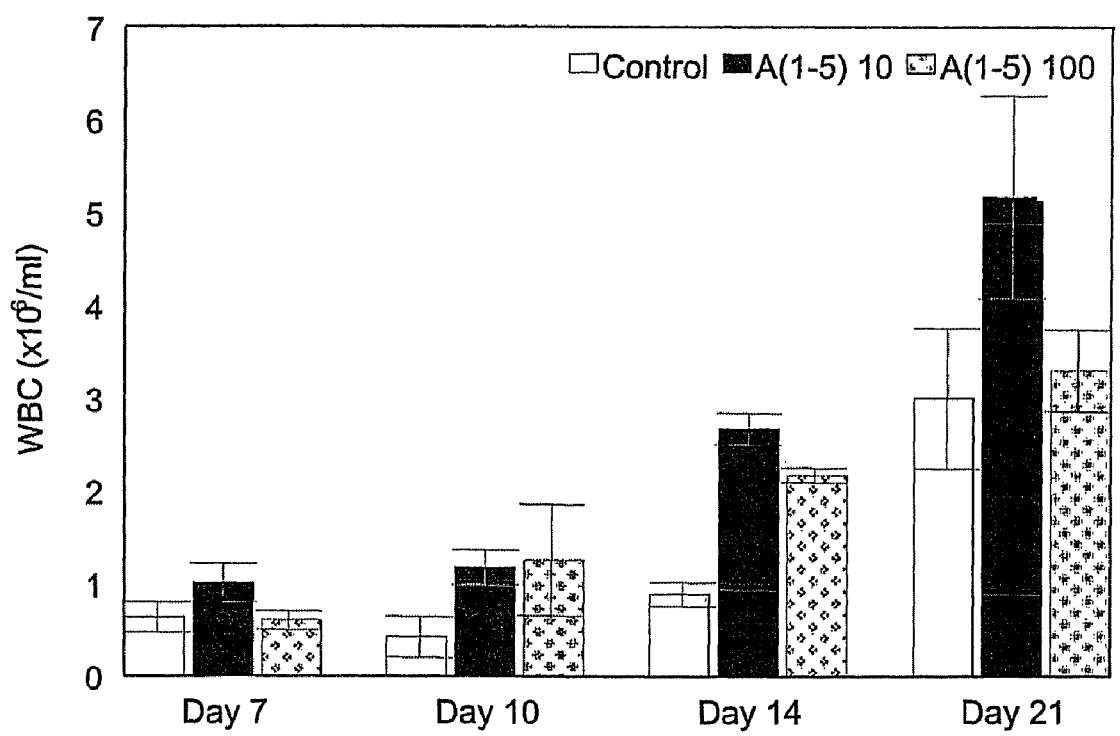
FIG. 35. Effect of AII analogues and enalapril on the increase in white blood cells in the peripheral blood after intravenous administration of 5FU.

These studies showed that all of the active agents tested increased the number of white blood cells in the peripheral blood after intravenous administration of 5FU (FIGS. 33-35). The decrease in WBC number as a result of administration of 5FU reached approximately 84%. The increase in WBC number was observed within 7 days after 5FU treatment (within 5 days after initiation of peptide administration). The increase in WBC continued throughout the experimental period but varied with the active agent. AII led to the most profound effect on this parameter followed by AII(1-7) and AII(1-5). AII(1-6) and enalapril were the least effective.

Figure 36:
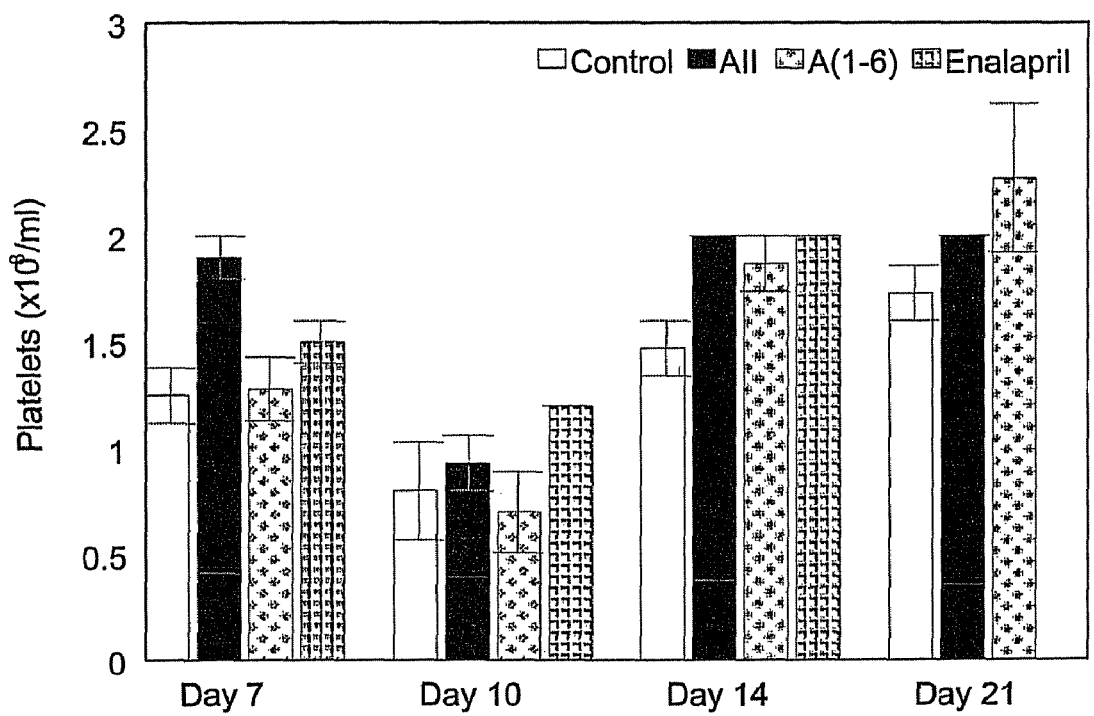
FIG. 36. Effect of AII analogues and enalapril on platelet increase after intravenous administration of 5FU.
Figure 37:
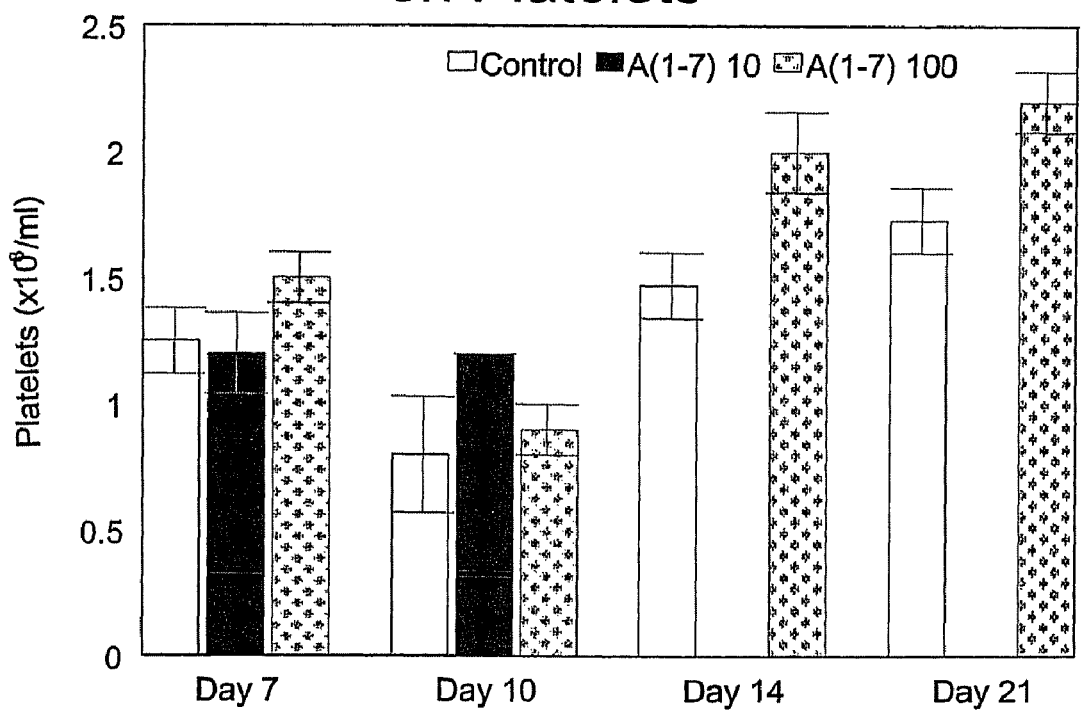
FIG. 37. Effect of AII analogues and enalapril on platelet increase after intravenous administration of 5FU.
Figure 38:
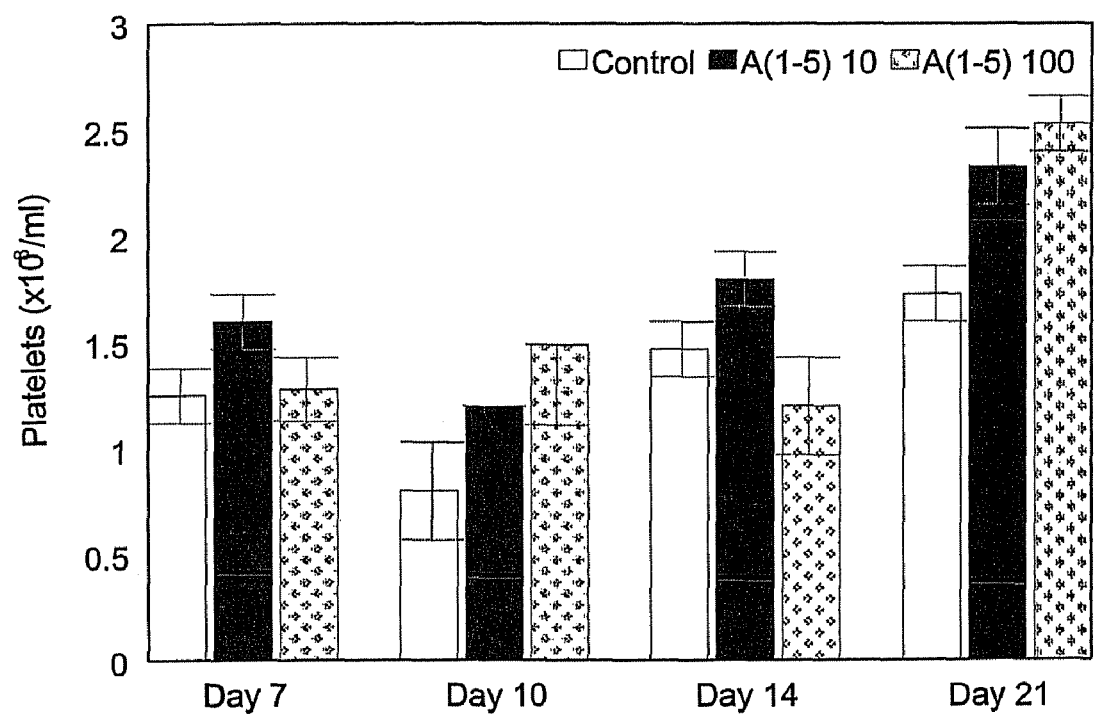
FIG. 38. Effect of AII analogues and enalapril on platelet increase after intravenous administration of 5FU.

Further, there was also an increase in platelets after administration of both AII(1-7) and AII(1-5) (FIGS. 36-38). Intravenous administration 5FU resulted in approximately a 70% decrease in platelet number that was maximal at day 10. Increases in platelet number occurred on days 14 and 21 with all test articles increasing the concentration of platelets in the blood.

Figure 39:
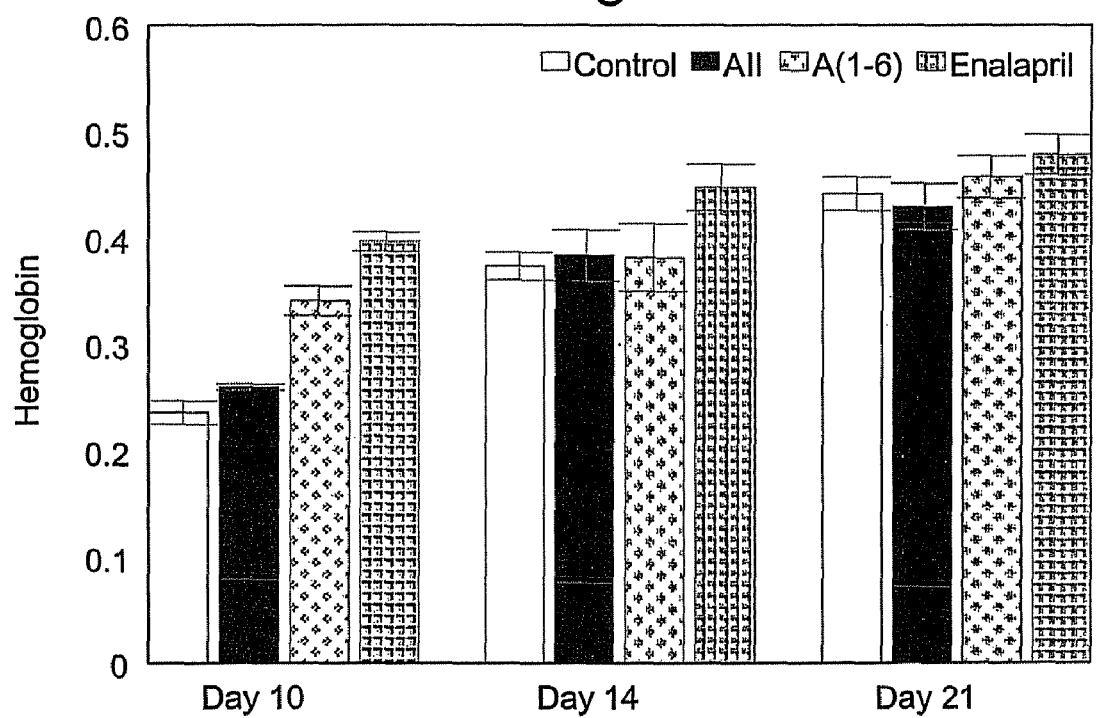
FIG. 39. Effect of AII analogues and enalapril on hemoglobin increase after intravenous administration of 5FU.
Figure 40:
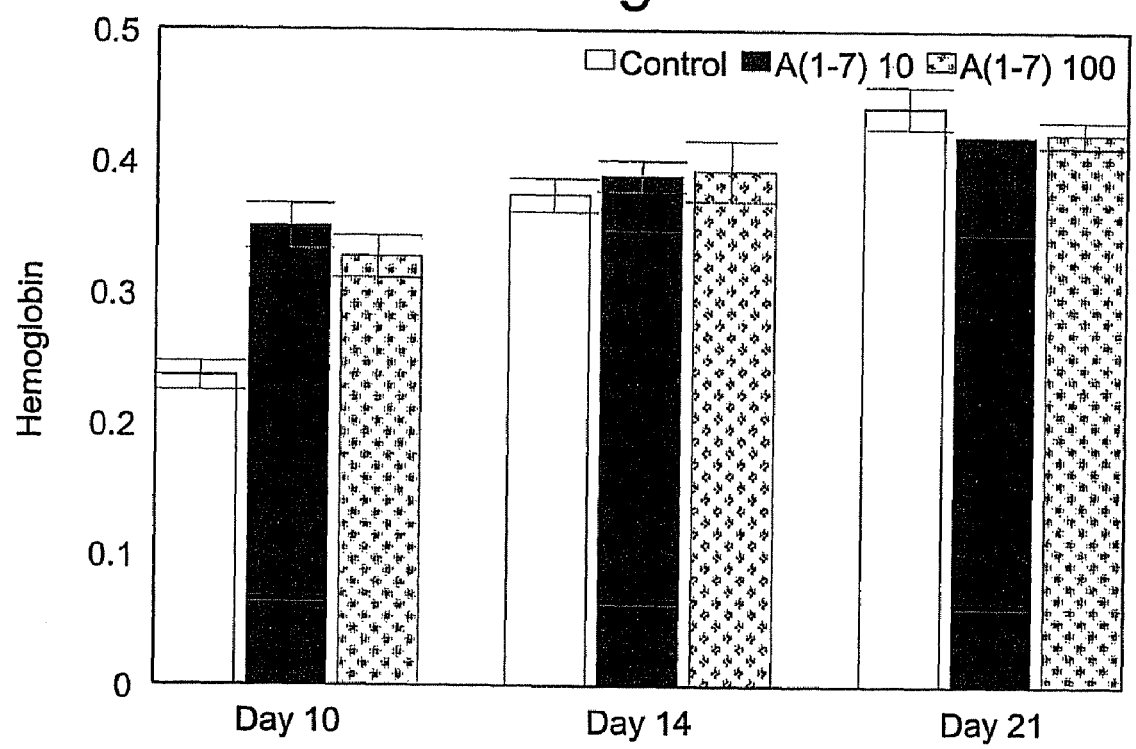
FIG. 40. Effect of AII analogues and enalapril on hemoglobin increase after intravenous administration of 5FU.
Figure 41:
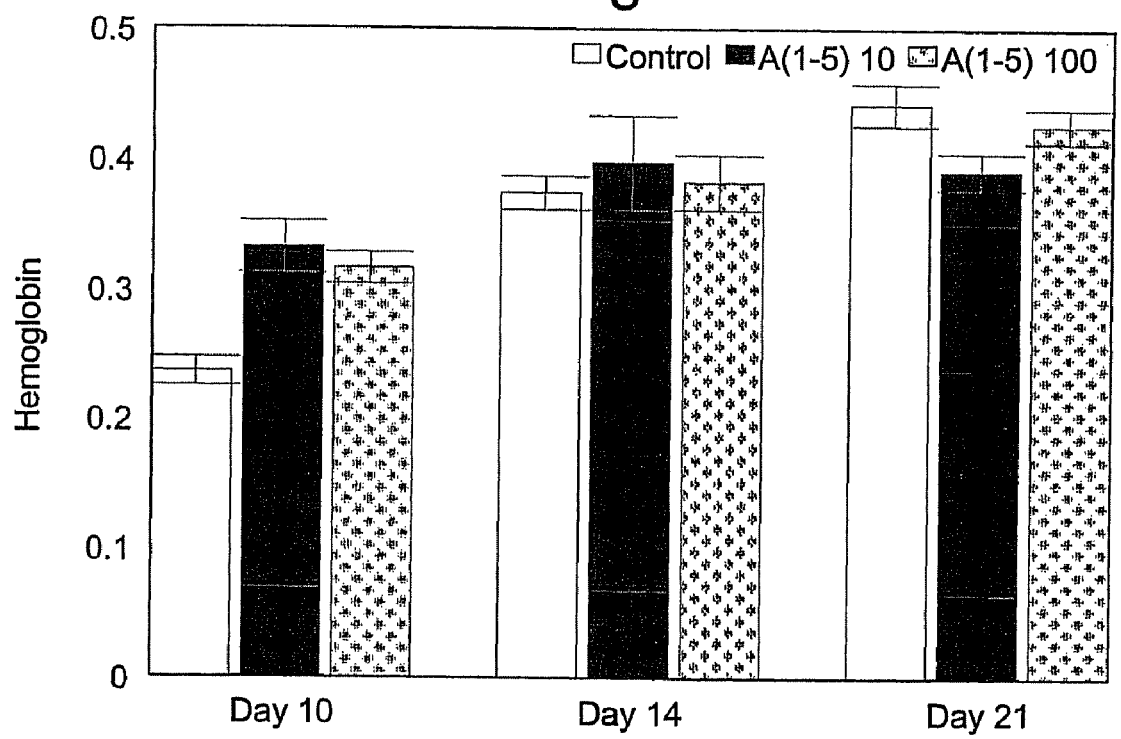
FIG. 41. Effect of AII analogues and enalapril on hemoglobin increase after intravenous administration of 5FU.

An increase in the level of hemoglobin in the blood was observed with all active agents, except AII, on day 10 (the nadir in control animals in this parameter). Thereafter, no further effect was observed (FIGS. 39-41).

In summary, all active agents tested accelerated the recovery of white blood cells, platelet number, and hemoglobin level after chemotherapy.

Example 5

Phase I/II Dose Escalation Study of AII(1-7) (SEQ ID NO:4) Administered Before and After Chemotherapy in Patients with Newly Diagnosed Breast Cancer Delivery of optimal dosing of cytotoxic chemotherapy is often limited by myelosuppression. Erythropoietin, filgrastim (G-CSF), sargramostim (GM-CSF), and oprelvekin (IL-11) have been the first recombinant hematopoietic growth factors to be United States Food and Drug Administration approved to stimulate human blood production and mitigate the toxicities of cytotoxic chemotherapy. There are a number of additional hematopoietic regulatory molecules that have been identified and are being produced in sufficient quantities to permit clinical testing in humans.

Data derived from pre-clinical studies demonstrated the effectiveness of AII(1-7) (SEQ ID NO:4) in accelerating hematopoietic recovery following chemotherapy induced myelosuppression. Additional activity on bone marrow and peripheral blood progenitor mobilization and proliferation was demonstrated with AII(1-7) indicating a potential for clinical utility following myelosuppressive cancer therapies. The pharmacologic effects appear to be multi-lineage and dose dependent.

The hematopoietic properties demonstrated in the preclinical studies support the investigation into the usefulness of AII(1-7) to decrease the incidence and severity of complications associated with myelosuppression secondary to cytotoxic therapy.

Based upon safety evaluation studies in animals (where the daily doses tested ranged from 10 to 1,000 µg/kg for 30 days) and the pharmacology profile of AII(1-7), the dose range used in humans ranged from 2.5 to 100 µg/kg/day over at least 10 days. This provided for an approximate 9-10 fold safety margin over the animal exposures.

Study Objectives

Primary Objectives
a) Determine the optimal biologic dose (OBD) or maximum tolerated dose (MTD) of AII(1-7) in cancer patients before and after treatment with cytotoxic therapy.

Secondary Objectives
a) Assess the hematologic profile in time to nadir, nadir, and time to recovery (absolute neutrophil count (ANC) >500 cells/µL and platelets>25,000/µL) in patients treated with AII(1-7) after treatment with chemotherapy.
b) Assess the mobilization of CD34+ progenitor cells and colony forming units (CFU-GM and CFU-GEMM) in peripheral blood after AII(1-7) treatment given before and after treatment with cytotoxic chemotherapy.
c) Assess the pharmacokinetic profile of AII(1-7) treatment given before treatment with cytotoxic therapy.
d) Assess the incidence and days of hospitalization, febrile neutropenia (>38.2° C. and ANC<1000 µL), and days of antibiotic use compared to filgrastim.
e) Assess the influence of AII(1-7) on the chemotherapy regimen (disease free survival (DFS) and overall survival (OS)).
f) Assess any synergy in hematologic response with AII(1-7) in combination with filgrastim.

Investigational Plan

This study compared the effects of AII(1-7) (SEQ ID NO:4) in patients with newly diagnosed breast cancer receiving doxorubicin 60 mg/m² and cyclophosphamide 600 mg/m² for at least 3 cycles of adjuvant chemotherapy following surgical tumor reduction. A filgrastim (recombinant G-CSF) (NEUPOGEN®, Amgen, Inc., Thousand Oaks, Calif.) comparator arm was used to compare safety and response variables and to assess synergy of AII(1-7) (SEQ ID NO:4) with filgrastim.

Dose Escalation Scheme

Patients who satisfied the inclusion/exclusion criteria received a once daily subcutaneous injection of the given AII(1-7) dose level for 7 days followed by a 1 week rest period prior to any chemotherapy (cycle 0), in order to permit evaluation of potential side effects of AII(1-7) in the absence of toxicity due to chemotherapy. Dose escalation within an individual patient was not be permitted. Dose escalation proceeded based on the occurrence of dose limiting toxicity (DLT).

Post Chemotherapy Studies

Following a rest period of 7 days, a chemotherapy regimen containing doxorubicin 60 mg/m² and cyclophosphamide 600 mg/m² was initiated. AII(1-7) was administered for at least 10 days, or until the ANC>1500 µL for 2 days, beginning two days after chemotherapy. Up to three chemotherapy cycles followed by AII(1-7) administration were repeated every 21 days or as indicated by patient tolerance. Any patient that failed to achieve an ANC>1500/µL by day 15 (13 days of AII(1-7)) received filgrastim at 5.0 µg/kg/day until the ANC>1500/µL for 2 days. Dosing began with the lowest dose of AII(1-7). In combination with each dosing group of AII(1-7), one additional patient received filgrastim 5.0 µg/kg/day beginning two days after chemotherapy and continuing for at least 10 days or until the ANC>1500/µL for 2 days. These patients were used for comparison with the AII(1-7) treated patients. Any patient in the AII(1-7) dosing arm that experienced an episode of febrile neutropenia following chemotherapy or failed to achieve an ANC>1500/µL during the first cycle received filgrastim at 5.0 µg/kg/day in combination with AII(1-7) for the remaining chemotherapy cycles. The remaining cycles for that patient were treated with filgrastim off protocol as determined by the Investigator. Patients received supportive treatment consistent with the standard of care as determined by the Investigator.

Endpoints

The primary safety endpoints were the incidence and grade of toxicity experienced by each dose group (DLT), MTD or OBD, changes in biochemistry, hematology, urinalysis, physical findings, and adverse events. Secondary safety endpoints were DFS and OS.

The preliminary efficacy endpoints were time to nadir (i.e.: the low point), nadir, and hematologic recovery (ANC> 500/µL and platelets>25,000/µL), mobilization of CD34+ progenitor cells, CFU-GM and GEMM after AII(1-7) (SEQ ID NO:4) treatment given before and after cytotoxic chemotherapy, and incidence and number of days of febrile neutropenia (>38.2° C.; ANC<1000 µL), hospitalization, infection, and antibiotic use.

Treatments

AII(1-7), filgrastim or both were self-administered following adequate patient training. AII(1-7) was administered once daily with a subcutaneous needle into a site located in the abdomen or thigh every morning.

Efficacy and Safety Variables

Hematology

Hematology assessment included red blood cell count (RBC), hemoglobin (Hgb), hematocrit (Hct), mean corpuscular volume (MCV), mean corpuscular hemoglobin (MCH), mean corpuscular hemoglobin concentration (MCHC), white blood cell count (WBC) including differential, reticulocyte count, and platelet count.

Coagulation

A coagulation panel was obtained for prothrombin time (PT) and activated partial thromboplastin time (PTT).

Adverse Event

An adverse event (AE) was considered as any unfavorable or unintended change in structure, function, signs, or symptoms temporally associated with the use of a medicinal product experienced by a person administered a pharmaceutical product, whether or not a causal relationship with the product was established. Clinically significant laboratory abnormalities were considered AEs if deemed appropriate by the Investigator. Worsening of a pre-existing condition was also considered an AE, as was the discovery of an abnormal finding during physical exam that was not included in the medical history.

Appropriateness of Measurements

The occurrence of febrile neutropenia was associated with significant morbidity and mortality in patients following myelosuppressive chemotherapy.

Primary Efficacy Variables

CD34+ assays

Peripheral blood was collected to conduct CD 34+ cell mobilization assays. Blood samples were obtained with a draw volume of 2 mL blood collection tubes.

Febrile Neutropenia

Patients were instructed to notify the Investigator of any oral temperature ≧38.2° C. Patients had a CBC obtained anytime they present with fever. If the ANC was <1000 µL in conjunction with an oral temperature ≧38.2° C., two blood cultures for aerobic/anaerobic bacteria were obtained, drawn 15 minutes apart.

Drug Concentration Measurements

Pharmacokinetics samples for the measurement of AII(1-7) and AII were collected and centrifuged. The specimen was decanted into a plastic transfer vial and stored at −20° C. Blood samples were obtained with a draw volume of 5 mL.

Results:

Administration of AII(1-7) resulted in an increase in multiple hematopoietic lineages and mobilization of hematopoietic progenitors into the peripheral blood. A dose dependent increase in the level of nadir in the number of white blood cells and absolute neutrophil count and time to these nadirs was observed. This is consistent with an effect on the compound on myeloid recovery after chemotherapy. At the lower doses, administration of filgrastim was required on Day 15 to restore acceptable levels of WBC prior to the next chemotherapy cycle. However, only one to two doses were required to substantially increase WBC and ANC suggesting a priming of the bone marrow cells for response to differentiating colony stimulating factors and a cytokine sparing effect of AII(1-7).

An additional benefit of administration of AII(1-7) was the ability of all patients to maintain on cycle, full intensity chemotherapy. It is expected that, after the first cycle of chemotherapy, the full dose of chemotherapeutic drug would not be administered to the patient at the time that would be optimal for cancer therapy, due to a dose-limiting toxicity that requires resolution. However, AII(1-7) administration permitted the patients to maintain full intensity chemotherapy on cycle.

Further, administration of AII(1-7) resulted in a dose-dependent increase in platelets. At the lowest dose, the nadir in platelet number occurred on day 12 and platelet number recovered thereafter. At 50 μg/kg/day of AII(1-7), only day 12 showed any change in platelet number. At the next higher dose, no decrease in platelet number occurred. In fact, an early increase relative to baseline was observed. In contrast, patients that received filgrastim had a time dependent decrease in platelet number that was more pronounced in subsequent cycles of chemotherapy.

Administration of AII(1-7) also affected the correction of anemia following administration of chemotherapeutic drugs. It was expected that administration of the chemotherapeutic drug would reduce the blood hemoglobin levels, that this reduction would not be corrected within the chemotherapy cycle and that the anemia would get progressively worse. This was observed after administration of filgrastim in these patients. After administration of the lowest dose of AII(1-7), a reduction in hemoglobin was observed. Contrary to that expected after administration of the chemotherapeutic drug in the absence of an adjuvant, the hemoglobin level returned to baseline levels by the next cycle. At subsequent dose increases of AII(1-7), slight to no anemia was observed, but at all doses, restoration of hemoglobin prior to the next cycle was observed.

To date, 14 patients have been exposed to AII(1-7) at 4 dosages (2.5 μg/kg/d, 10 μg/kg/d, 50 μg/kg/d, 75 μg/kg/d, and 100 μg/kg/d). Cumulative doses of >1500 μg/kg have been reached. No acute affect on blood pressure following administration has been observed in patients with or without a history of hypertension. No dose-limiting toxicities have been observed with AII(1-7) and all study patients have received 100% dose intensive chemotherapy to date. Anemia correction with each cycle has been observed with doses as low at 2.5 μg/kg. No drug related serious adverse events have been observed. No cycle delays due to neutropenia have occurred, however, patients treated at 2.5 and 10 μg/kg have needed 1-2 doses of filgrastim at day 15 to treat grade 4 neutropenia as directed by the protocol. Of note is that following 10-12 days of AII(1-7), as little as 1 dose of filgrastim normalizes the neutrophil count indicating a possible synergy between filgrastim and AII(1-7).

AII(1-7) reduced the frequency of grade 2-4 thrombocytopenia, grade 2-4 anemia, and grade 3-4 lymphopenia compared to filgrastim. Filgrastim patients experienced a lower frequency of grade 3-4 neutropenia compared to AII(1-7), however, the frequency of grade 3-4 leukopenia was similar in both groups. The most prominent hematologic effect with AII(1-7) was the prevention of thrombocytopenia.

| Toxicity | Filgrastim | 2.5 μg/kg | 10 μg/kg | 50 μg/kg | 75 μg/kg | 100 μg/kg |
|---|---|---|---|---|---|---|
| Hgb <10 gm/dl | 60% | 66% | 33% | 0% | 0% | 0% |
| Platelet <80K/μl | 60% | 0% | 0% | 0% | 0% | 0% |
| Lymph <500/μl | 80% | 66% | 33% | 33% | 0% | 0% |
| ANC <1000/μl | 40% | 100% | 100% | 100% | 100% | 100% |
| WBC <2000/μl | 60% | 66% | 66% | 66% | 100% | 33% |

Hgb = hemoglobin
Lymph = lymphocyte
ANC = Absolute neutrophil count
WBC = white blood cells Additionally, AII(1-7) reduced the frequency of stomatitis by 30% of that observed with filgrastim treatment, as well as decreasing the frequency of a number of other common side effects of chemotherapy, such as headache, muscle pain, and alopecia, relative to both historical numbers and filgrastim controls.

| Treatment Group | Historic | AII(1-7) (n = 15) | Filgratim (n = 5) |
|---|---|---|---|
| Nausea | 90% | 93% | 100% |
| Fatigue | | 93% | 80% |
| Anemia | 22% | 7% | 60% |
| Vomiting | | 80% | 60% |
| Headache | | 26% | 60% |
| Stomatitis | 88% | 40% | 60% |
| Myalgia/Muscle-skeletal pain | | 53% | 60% |
| Alopecia | 77% | 46% | 40% |

In summary, the data demonstrate the following:

AII(1-7) is safe without observed dose limiting toxicities.

Doses of AII(1-7) greater than 10 µg/kg/day appear to be active; the optimal dosage range appears to be 50-75 µg/kg/day.

No over-production of formed blood elements occurs before or after chemotherapy.

AII(1-7) reduces the frequency of gradable anemia, lymphopenia, and thrombocytopenia compared to filgrastim treated patients.

Neutrophil nadirs are not affected by AII(1-7), but late recovery is enhanced compared to filgrastim.

AII(1-7) improves the recovery towards baseline in all formed blood elements and minimizes pre-cycle progressive pancytopenia associated with myelosuppressive chemotherapy.

It is to be understood that the invention is not to be limited to the exact details of operation, or to the exact compounds, compositions, methods, procedures or embodiments shown and described, as obvious modifications and equivalents will be apparent to one skilled in the art, and the invention is therefore to be limited only by the full scope of the appended claims.

We claim:

1. An improved method for multiple cycle chemotherapy in a human patient, wherein the improvement comprises administering to the human chemotherapy patient an amount effective of a polypeptide consisting of at least 5 amino acids of SEQ ID NO:4 to permit treatment of the human chemotherapy patient with at least the same chemotherapy dosage on a second or further chemotherapy cycle as on the first chemotherapy cycle.

2. The improved method of claim 1, wherein the polypeptide consists of the amino acid sequence of SEQ ID NO:4.

3. The improved method of claim 2, wherein the polypeptide is administered at a dosage of between 2.5 µg/kg/day and about 100 µg/kg/day.

4. The improved method of claim 2, wherein the polypeptide is administered at a dosage of between 10.0 µg/kg/day and about 100 µg/kg/day.

5. The improved method of claim 2 wherein the polypeptide is administered parenterally.

6. The improved method of claim 2 wherein the polypeptide is administered subcutaneously or intravenously.

7. The improved method of claim 2 wherein administration of the polypeptide is initiated either at the time chemotherapy is initiated, or subsequent to initiation of chemotherapy.

8. The improved method of claim 2 wherein the human chemotherapy patient is treated with one or both of doxorubicin and cyclophosphamide.

9. The improved method of claim 2 wherein the human chemotherapy patient is treated for 3 chemotherapy cycles.

10. The improved method of claim 2 wherein the method further comprises treating the human chemotherapy patient with a cytokine selected from the group consisting of granulocyte colony stimulating factor, granulocyte-macrophage-CSF, epidermal growth factor, interleukin 11, thrombopoietin, megakaryocyte development and growth factor, pixykines, stem cell factor, FLT-ligand, and interleukins 1, 3, 6, and 7.

11. The improved method of claim 1, wherein the polypeptide is administered at a dosage of between 2.5 µg/kg/day and about 100 µg/kg/day.

12. The improved method of claim 1, wherein the polypeptide is administered at a dosage of between 10.0 µg/kg/day and about 100 µg/kg/day.

13. The improved method of claim 1 wherein the polypeptide is administered parenterally.

14. The improved method of claim 1 wherein the polypeptide is administered subcutaneously or intravenously.

15. The improved method of claim 1 wherein administration of the polypeptide is initiated either at the time chemotherapy is initiated, or subsequent to initiation of chemotherapy.

16. The improved method of claim 1 wherein the human chemotherapy patient is treated with one or both of doxorubicin and cyclophosphamide.

17. The improved method of claim 1 wherein the human chemotherapy patient is treated for 3 chemotherapy cycles.

18. The improved method of claim 1 wherein the method further comprises treating the human chemotherapy patient with a cytokine selected from the group consisting of granulocyte colony stimulating factor, granulocyte-macrophage-CSF, epidermal growth factor, interleukin 11, thrombopoietin, megakaryocyte development and growth factor, pixykines, stem cell factor, FLT-ligand, and interleukins 1, 3, 6, and 7.

* * * * *